(12) United States Patent
Marar et al.

(10) Patent No.: US 10,493,001 B2
(45) Date of Patent: Dec. 3, 2019

(54) NASOGASTRIC EXPANDABLE INTUBATION ASSEMBLES

(71) Applicants: Taymoor Marar, Lyons (FR); Talal Sharaiha, New York, NY (US); Bertrand Basch, Soufflenheim (FR); Raymond Basch, Mothern (FR)

(72) Inventors: Taymoor Marar, Lyons (FR); Talal Sharaiha, New York, NY (US); Bertrand Basch, Soufflenheim (FR); Raymond Basch, Mothern (FR)

( * ) Notice: Subject to any disclaimer, the term of this patent is extended or adjusted under 35 U.S.C. 154(b) by 0 days.

(21) Appl. No.: 16/302,378

(22) PCT Filed: May 17, 2017

(86) PCT No.: PCT/US2017/033118
§ 371 (c)(1),
(2) Date: Nov. 16, 2018

(87) PCT Pub. No.: WO2017/201168
PCT Pub. Date: Nov. 23, 2017

(65) Prior Publication Data
US 2019/0282452 A1    Sep. 19, 2019

Related U.S. Application Data

(60) Provisional application No. 62/337,670, filed on May 17, 2016.

(51) Int. Cl.
*A61M 25/10* (2013.01)
*A61J 15/00* (2006.01)
*A61M 39/24* (2006.01)

(52) U.S. Cl.
CPC ....... *A61J 15/0049* (2013.01); *A61J 15/0003* (2013.01); *A61M 25/1011* (2013.01);
(Continued)

(58) Field of Classification Search
CPC .............. A61M 25/10; A61M 25/1002; A61M 25/1006; A61M 25/1011;
(Continued)

(56) References Cited

U.S. PATENT DOCUMENTS 4,637,396 A     1/1987  Cook
5,360,402 A  *  11/1994  Conway ................. A61L 29/06
                                                          604/915
(Continued)

OTHER PUBLICATIONS

International Search Report and Written Opinion of the International Searching Authority or the Declaration; dated Aug. 16, 2017.

*Primary Examiner* — Nathan R Price
*Assistant Examiner* — Justin L Zamory
(74) *Attorney, Agent, or Firm* — Pepper Hamilton LLP

(57) ABSTRACT

Embodiments can provide an expandable nasogastric intubation assembly, comprising a tube subassembly and an expander subassembly, comprising an inflatable balloon comprising a proximal expander component section and a distal expander component section wherein the proximal expander component section is located between the proximal end of the intubation assembly and the distal expander component section; wherein the distal expander component section is located between the distal end of the intubation assembly and the proximal expander component section; wherein the inflatable balloon is coupled to the tube subassembly, the proximal expander component section is configured to be inflated from an injection of fluid into at least one first opening located in the second passageway, and the distal expander component section is configured to be inflated by the injection of fluid into at least one second opening located in the second passageway.

14 Claims, 30 Drawing Sheets

(52) U.S. Cl.
CPC ............... *A61M 25/10186* (2013.11); *A61M 2025/1061* (2013.01); *A61M 2039/242* (2013.01)

(58) Field of Classification Search
CPC .......... A61M 25/10181; A61M 25/104; A61M 25/10186; A61M 16/04; A61M 16/0475; A61M 16/0477; A61M 16/0486; A61M 16/0465; A61M 16/0434; A61B 2017/22074; A61J 15/0049
See application file for complete search history.

(56) References Cited

U.S. PATENT DOCUMENTS

| | | | |
|---|---|---|---|
| 5,588,424 A * | 12/1996 | Insler | A61M 16/04 128/207.15 |
| 5,971,954 A * | 10/1999 | Conway | A61L 29/085 604/101.05 |
| 2003/0066532 A1 | 4/2003 | Gobel | |
| 2007/0203445 A1* | 8/2007 | Kaye | A61M 1/3653 604/6.16 |
| 2007/0295336 A1* | 12/2007 | Nelson | A61M 16/04 128/207.15 |
| 2009/0062725 A1 | 3/2009 | Goebel | |
| 2009/0062771 A1 | 3/2009 | Tarola et al. | |
| 2011/0028896 A1 | 3/2011 | Burnside et al. | |
| 2014/0276530 A1* | 9/2014 | Gianotti | A61M 25/1002 604/500 |
| 2016/0106939 A1 | 4/2016 | Sharaiha et al. | |

\* cited by examiner

NASOGASTRIC EXPANDABLE INTUBATION ASSEMBLIES

CROSS-REFERENCE TO RELATED APPLICATIONS

This application is a national phase filing under 35 U.S.C. § 371 of International Patent Application No. PCT/US2017/033118, filed May 17, 2017, which claims the benefit of U.S. Provisional Patent Application No. 62/337,670, filed May 17, 2016, each of which is incorporated herein by reference in its entirety.

TECHNICAL FIELD

This disclosure relates to expandable assemblies and, more particularly, to expandable intubation assemblies and methods for using and making the same.

BACKGROUND OF THE DISCLOSURE

Various medical procedures (e.g., intubation procedures) involve a distal end of a tube being inserted into a specific area of a patient and then using the tube for injecting material into the patient and/or for removing material from the patient. However, safely securing such a tube at a particular position within the patient during use has heretofore been infeasible. Moreover, safely preventing certain material from passing along the external surface of such a tube during use has heretofore been infeasible.

SUMMARY OF THE DISCLOSURE

This document describes expandable assemblies and methods for using and making the same.

This summary is provided merely to summarize some example embodiments, so as to provide a basic understanding of some aspects of the subject matter described in this document. Accordingly, it will be appreciated that the features described in this Summary are merely examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

Embodiments can provide an expandable nasogastric intubation assembly, comprising a tube subassembly, comprising at least one tube wall defining at least one internal passageway extending along at least a portion of the intubation assembly, the at least one tube wall comprising one or more surfaces that in conjunction with the at least one tube wall define a second passageway beginning at a closed end and extending to a second passageway access opening; a proximal tube opening located at a proximal end of the intubation assembly; and a distal tube opening located at a distal end of the intubation assembly; wherein the passageway access opening is radially adjacent to the proximal tube opening; an expander subassembly, comprising an inflatable balloon comprising a proximal expander component section and a distal expander component section wherein the proximal expander component section is located between the proximal end of the intubation assembly and the distal expander component section; wherein the distal expander component section is located between the distal end of the intubation assembly and the proximal expander component section; wherein the inflatable balloon is coupled to the tube subassembly, the proximal expander component section is configured to be inflated from an injection of fluid into at least one first opening located in the second passageway, and the distal expander component section is configured to be inflated by the injection of fluid into at least one second opening located in the second passageway.

Embodiments can further provide an assembly wherein the distal expander component section has a cross-sectional dimension greater than a cross-sectional dimension of the proximate expander component section.

Embodiments can further provide an assembly wherein the proximal expander component section and the distal expander component section are separated by a non-expanding portion of the at least one tube wall.

Embodiments can further provide an assembly wherein the proximal expander component section and the distal expander component section are separated by an intermediate expander component section;

wherein the intermediate expander component section is constricted such that the intermediate expander component section has a cross-sectional dimension less than that of the proximate expander component section.

Embodiments can further provide an assembly wherein the injected fluid is air.

Embodiments can further provide an assembly wherein the expander subassembly further comprises at least one one-way valve located between the proximal expander component section and the distal expander component section; wherein when one or more patient walls contract against the expander subassembly the injectable fluid flows from the proximal expander component section into the distal expander component section.

Embodiments can further provide an assembly with the expander subassembly further comprising at least one second one-way valve on the at least one second opening located on the second passageway; wherein when one or more patient walls contract against the proximal expander component section the injectable fluid flows from the distal expander component section through the second passageway and into the proximal expander component section.

Embodiments can further provide an assembly with the tube assembly further comprising a burst valve located across the passageway access opening; wherein the burst valve is configured to release if the proximal expander component section and the distal expander component section are inflated to a maximum cross-sectional dimension and one or more patient walls contract against the expander subassembly.

Embodiments can further provide an assembly with the tube assembly further comprising a supplemental tube passageway embedded within the at least one tube wall.

Embodiments can further provide an expandable nasogastric intubation assembly, comprising a tube subassembly, comprising at least one tube wall defining at least one internal passageway extending along at least a portion of the intubation assembly, the at least one tube wall comprising one or more surfaces that in conjunction with the at least one tube wall define a second passageway beginning at a closed end and extending to a second passageway access opening; a proximal tube opening located at a proximal end of the intubation assembly; and a distal tube opening located at a distal end of the intubation assembly; wherein the passageway access opening is radially adjacent to the proximal tube opening; an expander subassembly coupled to the tube subassembly, comprising a proximal expander component comprising a first limiting mechanism secured to an end of the proximal expander component and a portion of the at least one tube wall; a distal expander component comprising a second limiting mechanism secured to an end of the distal expander component and a portion of the at least one tube wall; wherein the proximal expander component is located between the proximal end of the intubation assembly and the distal expander component; wherein the distal expander component is located between the distal end of the intubation assembly and the proximal expander component; wherein the proximal expander component is configured to be inflated from an injection of fluid into at least one first opening located in the second passageway, and the distal expander component is configured to be inflated by the injection of fluid into at least one second opening located in the second passageway.

Embodiments can further provide an assembly wherein the distal expander component has a cross-sectional dimension greater than a cross-sectional dimension of the proximal expander component.

Embodiments can further provide an assembly wherein the proximal expander component and the distal expander component are separated by a length of non-expanding tube wall.

Embodiments can further provide an assembly wherein the injected fluid is air.

Embodiments can further provide an assembly wherein when one or more patient walls contract against the proximal expander component the injectable fluid flows from the proximal expander component into the distal expander component; and wherein when one or more patient walls contract against the distal expander component the injectable fluid flows from the distal expander component through the second passageway and into the proximal expander component.

Embodiments can further provide an assembly with the tube assembly further comprising a burst valve located across the passageway access opening; wherein the burst valve is configured to release if the proximal expander component and the distal expander component are inflated to a maximum cross-sectional dimension and one or more patient walls contract against the expander subassembly.

Embodiments can further provide an assembly with the tube assembly further comprising a supplemental tube passageway embedded within the at least one tube wall.

BRIEF DESCRIPTION OF THE DRAWINGS

The discussion below makes reference to the following drawings, in which like reference characters may refer to like parts throughout, and in which.

DETAILED DESCRIPTION OF THE DISCLOSURE

Figure 1:
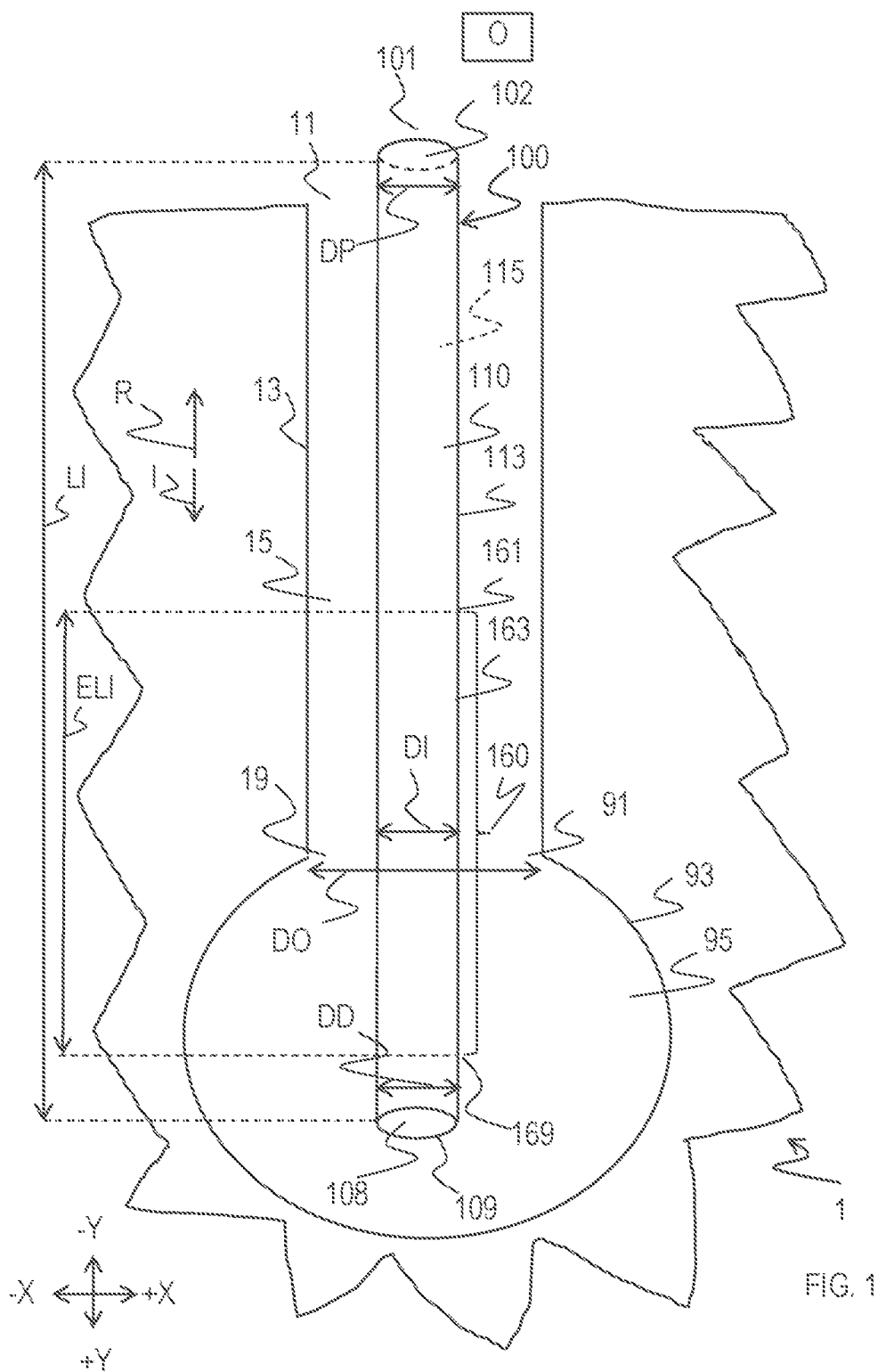
FIG. 1 is a cross-sectional view of a patient with an intubation assembly in an insertion state.
Figure 1A:
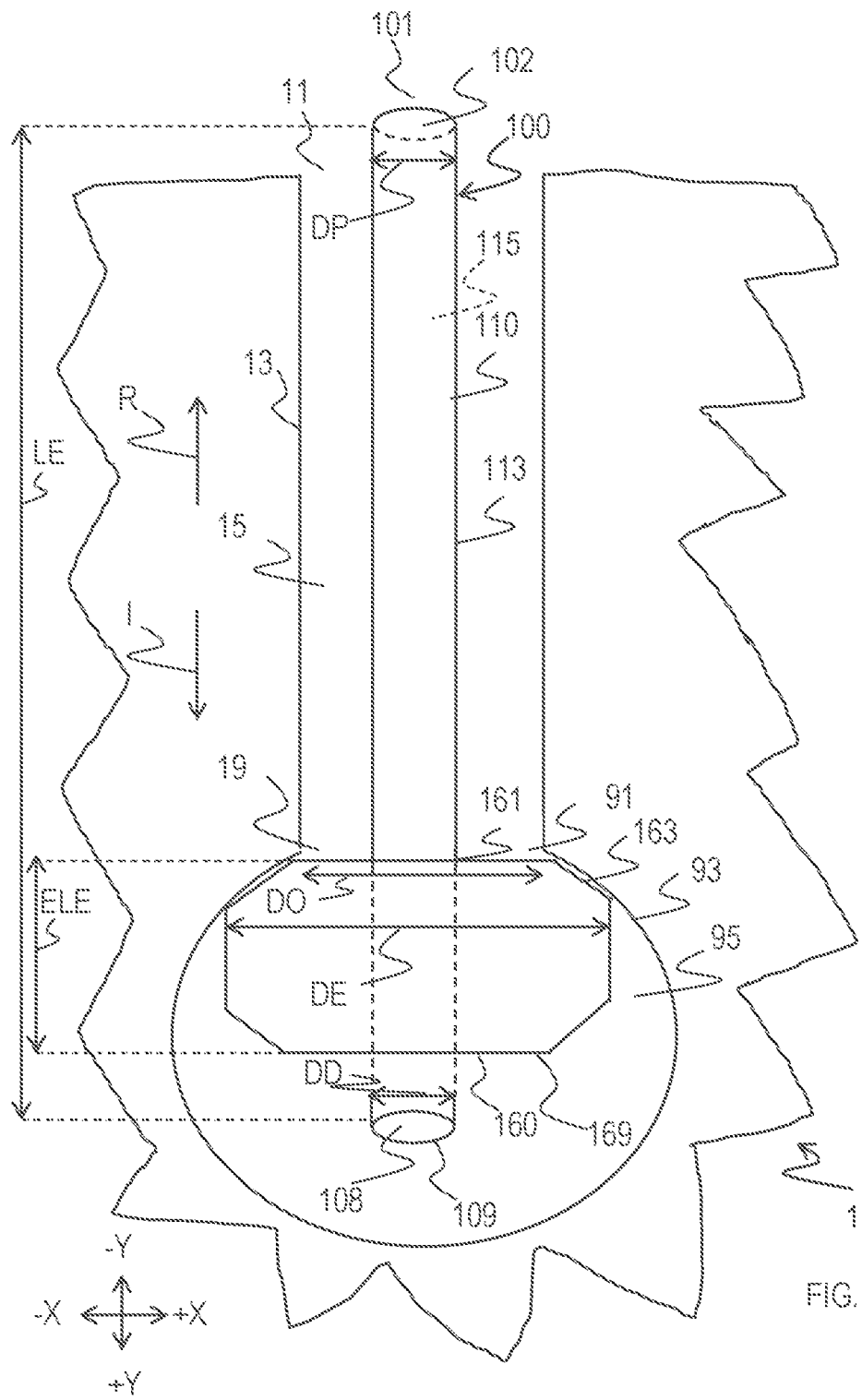
FIGS. 1A-1C are cross-sectional views, similar to FIG. 1, of the patient of FIG. 1 with the intubation assembly of FIG. 1 in various illustrative expanded states.
Figure 1B:
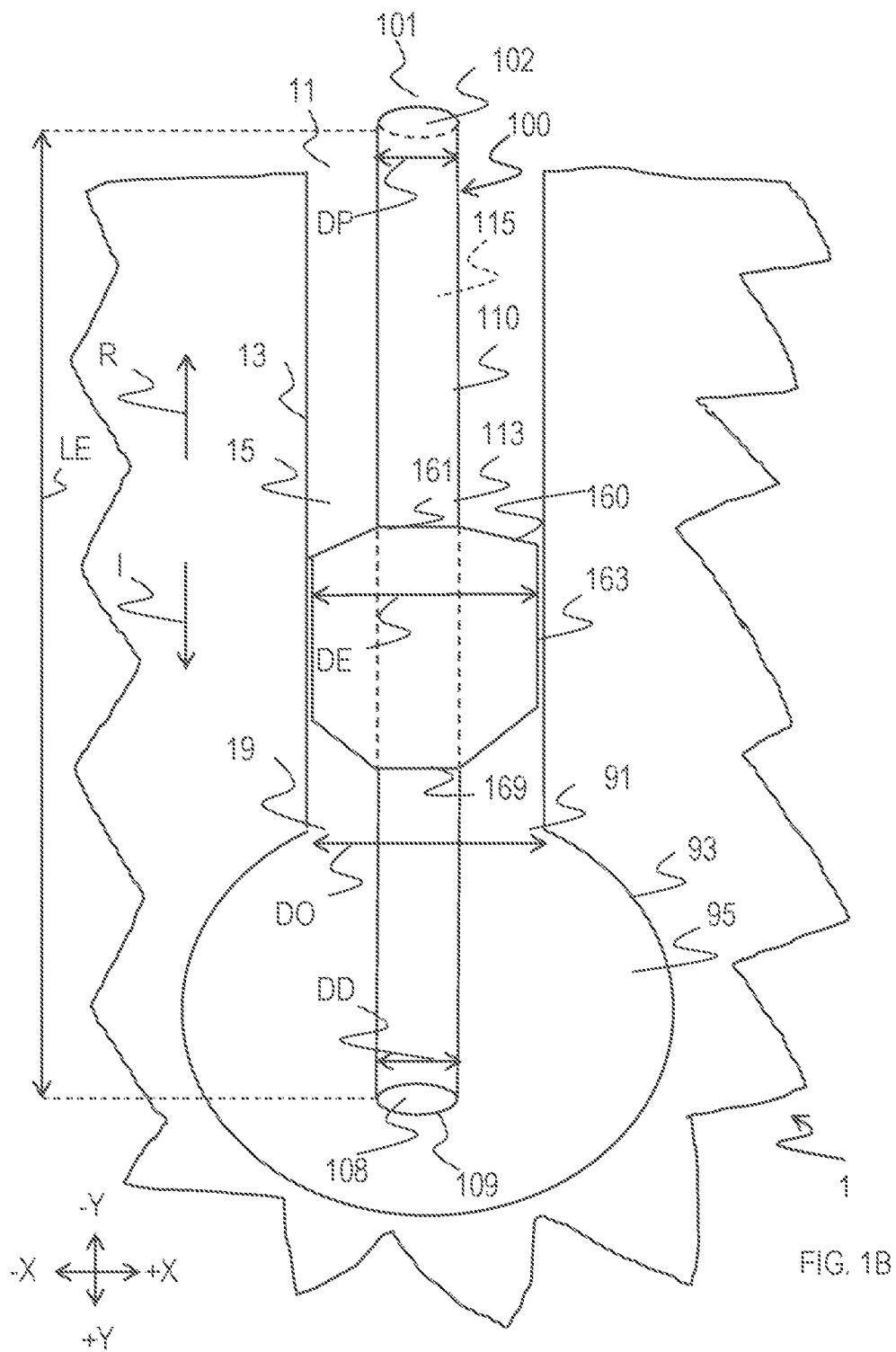
Figure 1C:
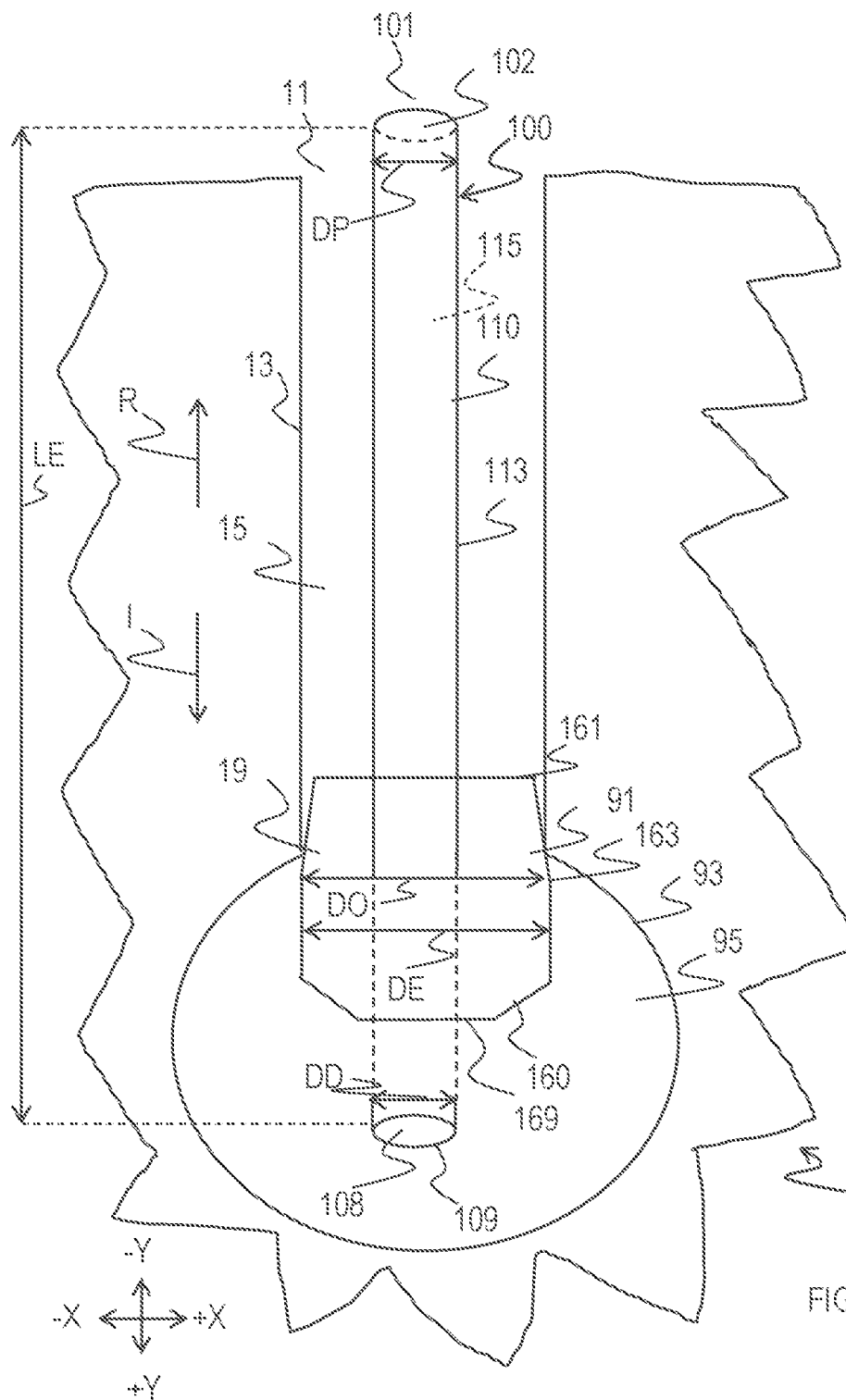
Figure 1D:
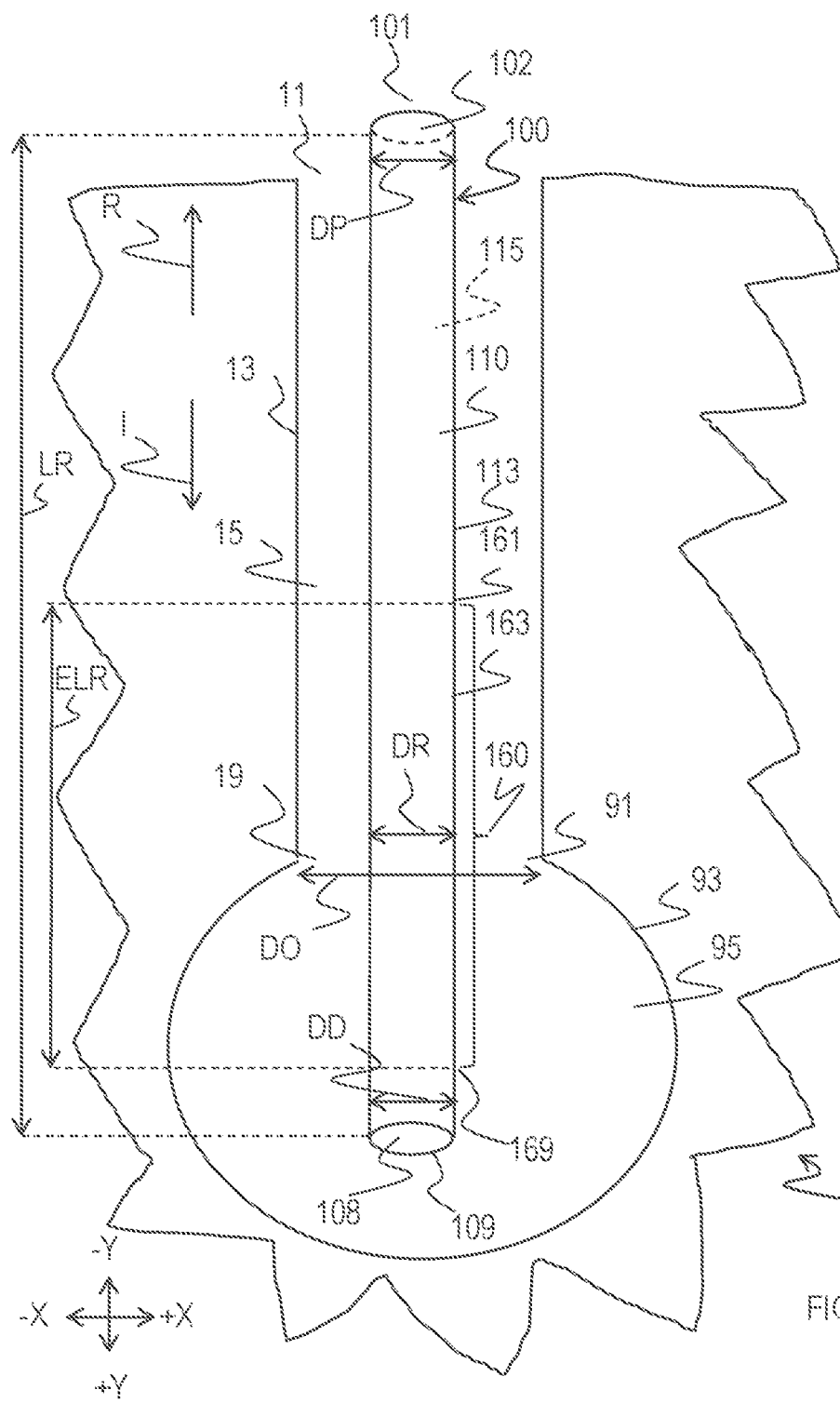
FIG. 1D is a cross-sectional view, similar to FIGS. 1-1C, of the patient of FIGS. 1-1C with the intubation assembly of FIGS. 1-1C in a removal state.

FIGS. 1-1D show an illustrative assembly 100 in various configurations or stages of use with respect to a patient 1. Assembly 100 may be an intubation assembly or any other suitable assembly for use in any suitable procedure with respect to any suitable patient 1. As shown in FIGS. 1-1D, for example, assembly 100 may extend between a proximal or first assembly end 101, which may have an outer cross-sectional dimension (e.g., diameter) DP, and a distal or second assembly end 109, which may have an outer cross-sectional dimension (e.g., diameter) DD. Assembly 100 may include at least one tube or tube subassembly 110 that may extend between ends 101 and 109. Tube subassembly 110 may include at least one tube wall 113 that may define at least one internal passageway 115 extending along at least a portion of assembly 100. Wall 113 may also include at least one proximal or first tube opening 102 that may provide access to passageway 115 at or near end 101 of assembly 100 and at least one distal or second tube opening 108 that may provide access to passageway 115 at or near end 109 of assembly 100. Moreover, assembly 100 may also include an expander or expander subassembly 160 that may extend along at least a portion of tube subassembly 110, where expander subassembly 160 may include an external surface 163. As also shown in FIGS. 1-1D, for example, patient 1 may include a passageway wall 13 that may define a passageway 15 that may extend between at least one proximal or first access opening 11 and a distal or second opening 19. Moreover, patient 1 may include a target wall 93 that may define at least a portion of a target space 95, where a proximal or first target opening 91 of wall 93 may be coupled to opening 19 of passageway 15, such that passageway 15 may be fluidly coupled to target space 95. As shown in FIGS. 1-1D, for example, at least a portion of passageway 15 and/or the coupling of opening 19 and opening 91 may have a cross-sectional dimension (e.g., diameter) DO, which may be a minimum dimension of patient 1 through which at least a portion of assembly 100 may pass or otherwise exist during any stage of use within patient 1.

When in an insertion state (see, e.g., FIG. 1), assembly 100 may be inserted into patient 1 to a particular position, and then assembly 100 may be re-configured into an expanded state (see, e.g., FIG. 1A and/or FIG. 1B and/or FIG. 1C) within patient 1 such that assembly 100 may be safely used within patient 1. After use of assembly 100 in its expanded state within patient 1, assembly 100 may be re-configured into a removal state (see, e.g., FIG. 1D) within patient 1 for removal of assembly 100 from patient 1. For example, as shown by FIG. 1, assembly 100 may first be configured in an insertion state or configuration such that assembly 100 may then be at least partially inserted into patient 1. In some embodiments, end 109 of assembly 100 in its insertion state may be inserted into patient 1 in the direction of arrow I through opening 11, through passageway 15, through opening 19, through opening 91, and into target space 95, such that at least one opening 108 of assembly 100 may be within space 95 and/or such that at least one opening 102 of assembly 100 may be accessible to an operator O of assembly 100 (e.g., a physician or nurse or perhaps even patient 1 itself), who may be external to at least passageway 15 of patient 1. Assembly 100 may be of a length LI that may extend between end 101 and end 109 of assembly 100 in its insertion state, and where such a length provided by assembly 100 in its insertion state may vary based on the size of patient 1 and the procedure to be performed. As shown in FIG. 1, when assembly 100 is in its insertion state, no portion of expander 160 may have a cross-sectional dimension (e.g., diameter) greater than dimension DI. In some embodiments, dimension DD of end 109 and dimension DI of expander 160 in the insertion state of assembly 100 may be less than dimension DO of patient 1 such that assembly 100 in its insertion state may be safely inserted into patient 1 without damaging wall 13 and/or wall 93 of patient 1.

After assembly 100 has been inserted into patient 1 while assembly 100 is in its insertion state, assembly 100 may be re-configured into an expanded state within patient 1 such that assembly 100 may thereafter be safely used within patient 1. For example, as shown in each one of FIGS. 1A-1C, once assembly 100 in its insertion state has been inserted into its insertion position of FIG. 1 within patient 1, assembly 100 may be re-configured into an expanded state within patient 1 such that assembly 100 may thereafter be safely used in that expanded state within patient 1. As shown in each one of FIGS. 1A-1C, when assembly 100 is in its expanded state, at least a portion of expander 160 may have a maximum cross-sectional dimension (e.g., diameter) DE that may be at least equal to or greater than dimension DO of patient 1, such that at least a portion of wall 163 of expander 160 may contact or otherwise interact with at least a portion of wall 93 of target 95 and/or with at least a portion of wall 13 of passageway 15 for safely securing expanded assembly 100 at a particular position within patient 1 and/or for safely preventing certain material from traveling between wall 163 of expander 160 and at least a portion of wall 93 of target 95 and/or at least a portion of wall 13 of passageway 15. One or more of dimensions DE, DI, and DR (e.g., as described below) may be widths defined by expander 160, where such a width may be perpendicular to the length of expander 160 (e.g., along the X-axis, which may be perpendicular to the length extending between ends 161 and 169 of expander 160 along the Y-axis). As shown in FIG. 1A, for example, all of expander 160 may be positioned within target space 95 when assembly 100 is re-configured from its insertion state into its expanded state, such that at least a portion of wall 163 of expander 160 may contact or otherwise interact with at least a portion of wall 93 of target 95. Alternatively, as shown in FIG. 1B, for example, all of expander 160 may be positioned within passageway 15 when assembly 100 is re-configured from its insertion state into its expanded state, such that at least a portion of wall 163 of expander 160 may contact or otherwise interact with at least a portion of wall 13 of passageway 15. Alternatively, as shown in FIG. 1C, for example, a first portion of expander 160 may be positioned within passageway 15 and a second portion of expander 160 may be positioned with target space 95 when assembly 100 is re-configured from its insertion state into its expanded state, such that at least a first portion of wall 163 of expander 160 may contact or otherwise interact with at least a portion of wall 13 of passageway 15 and such that at least a second portion of wall 163 of expander 160 may contact or otherwise interact with at least a portion of wall 93 of target 95. As shown in FIGS. 1A-1C, at least a portion of expander 160 may expand at least along the X-axis such that a maximum cross-sectional dimension (e.g., diameter) of expander 160 may expand from dimension DI to dimension DE when assembly 100 is reconfigured from its insertion state to its expanded state. As shown in FIGS. 1A-1C, assembly 100 may be of a length LE that may extend between end 101 and end 109 of assembly 100 in its expanded state, where such a length LE provided by assembly 100 may vary based on the size of patient 1 and may be greater than, less than, or equal to length LI of assembly 100 in its insertion state (e.g., the state of FIG. 1) and/or length LR of assembly 100 in its removal state (e.g., the state of FIG. 1D, described below).

Once assembly 100 has been expanded into its expanded state within patient 1 (e.g., as shown in any one or more of FIGS. 1A-1C), assembly 100 may be safely used within patient 1 in any suitable way, such as in any suitable intubation process. For example, in some embodiments, expanded assembly 100 may be safely used within patient 1 for injecting material (e.g., treatment material, such as nutrients or medicine or oxygen) through opening 102, into and through passageway 115, then out of passageway 115 through opening 108, and into target space 95 of patient 1, and/or for removing material (e.g., treatment material, such as waste) from target space 95, through opening 108, into and through passageway 115, then out of passageway 115 through opening 102 away from patient 1. In certain embodiments, target space 95 may be a stomach, opening 91 may be a lower esophageal sphincter, passageway 15 may be an esophagus, pharynx, throat, and/or nasal cavity, and opening 11 may be a nostril or mouth of patient 1, where assembly 100 may be used during a nasogastric intubation process. In other embodiments, target space 95 may be a bladder, opening 91 may be a sphincter, passageway 15 may be a urethra, and opening 11 may be a urinary meatus of patient 1, where assembly 100 may be used during any suitable process that might otherwise use a Foley catheter. It is to be understood that assembly 100 may be used with respect to any suitable portions of any suitable patient 1 for any suitable process, where expander 160 may be expanded such that at least a portion of wall 163 of expander 160 may contact or otherwise interact with at least a portion of wall 93 of target 95 and/or with at least a portion of wall 13 of passageway 15 for safely securing expanded assembly 100 at a particular position within patient 1 (e.g., for preventing opening 108 and/or end 109 of assembly 100 from being inadvertently removed from target space 95 (e.g., in the direction of arrow R) and/or from being inadvertently inserted too far into space 95 (e.g., in the direction of arrow I), such as when assembly 100 may be used as a Foley catheter) and/or for safely preventing certain material from traveling between wall 163 of expander 160 and at least a portion of wall 93 of target 95 and/or between wall 163 of expander 160 and at least a portion of wall 13 of passageway 15 (e.g., for preventing contents of a stomach target 95 from escaping target 95 through passageway 15 about the exterior of wall 163 of expander 160 (i.e., not through assembly 100), such as towards a trachea or other portion of patient 1 between expander 160 and end 11 of passageway 15 that may cause infections and/or inflammation (e.g., in the direction of arrow R), such as when assembly 100 may be used as a nasogastric tube). Specifically, reflux of contents from the stomach back into the esophagus has been a persistent problem, especially in the presence of nasogastric tubes. Contents often attempt to travel back up from the stomach around the tube, thereby causing reflux esophagitis, aspiration pneumonitis, and/or pneumonias.

After assembly 100 has been used in its expanded state within patient 1, assembly 100 may be re-configured into a removal state such that assembly 100 may thereafter be safely removed from within patient 1 (e.g., in the direction of arrow R). For example, as shown in FIG. 1D, once assembly 100 has been used in its expanded state of any of FIGS. 1A-1C within patient 1, assembly 100 may be re-configured into a removal state within patient 1 such that assembly 100 may thereafter be safely removed in its removal state from within patient 1. For example, as shown in FIG. 1D, when assembly 100 is in its removal state, no portion of expander 160 may have a cross-sectional dimension (e.g., diameter) greater than dimension DR, where such a dimension DR provided by assembly 100 may vary based on the size of patient 1 and may be greater than, less than, or equal to dimension DI of the insertion state. In some embodiments, dimension DD of end 109 and dimension DR of expander 160 in the removal state of assembly 100 may be less than dimension DO of patient 1 such that assembly 100 in its removal state may be safely removed from patient 1 without damaging wall 13 and/or wall 93 of patient 1. In some embodiments, as shown in FIG. 1D, at least a portion of expander 160 may contract at least along the X-axis such that a maximum cross-sectional dimension (e.g., diameter) of expander 160 may contract from dimension DE to dimension DR when assembly 100 is reconfigured from its expanded state to its removal state. As shown in FIG. 1D, assembly 100 may be of a length LR that may extend between end 101 and end 109 of assembly 100 in its removal state, where such a length LR provided by assembly 100 may vary based on the size of patient 1 and may be greater than, less than, or equal to length LI of assembly 100 in its insertion state and/or length LE of assembly 100 in its expanded state. It is to be noted that, while "proximal" or "proximate" may be used herein to refer to a general direction or end of assembly 100 that may be closest to operator O of assembly 100 during use (e.g., external to patient 1), and while "distal" or "distant" may be used herein to refer to a general direction or end of assembly 100 that may be farthest from operator O of assembly 100 during use (e.g., within target 95), such directional and orientational terms may be used herein only for convenience, and that no fixed or absolute directional or orientational limitations are intended by the use of these words.

In some embodiments, expander subassembly 160 may include a balloon (e.g., a high volume, low pressure balloon) or any other suitable expander mechanism or component that may be inflatable by air or any other suitable fluid (e.g., gas or liquid or any other suitable substance that may be able to flow into and/or out of the expander mechanism) for enabling the expansion of at least a portion of expander subassembly 160 (e.g., from dimension DI to dimension DE), which may allow at least a portion of expander subassembly 160 to contact a wall of patient 1 for securing expanded assembly 100 at a particular position within patient 1 and/or for preventing certain material from traveling between expander subassembly 160 and a wall of patient 1.

Figure 2:
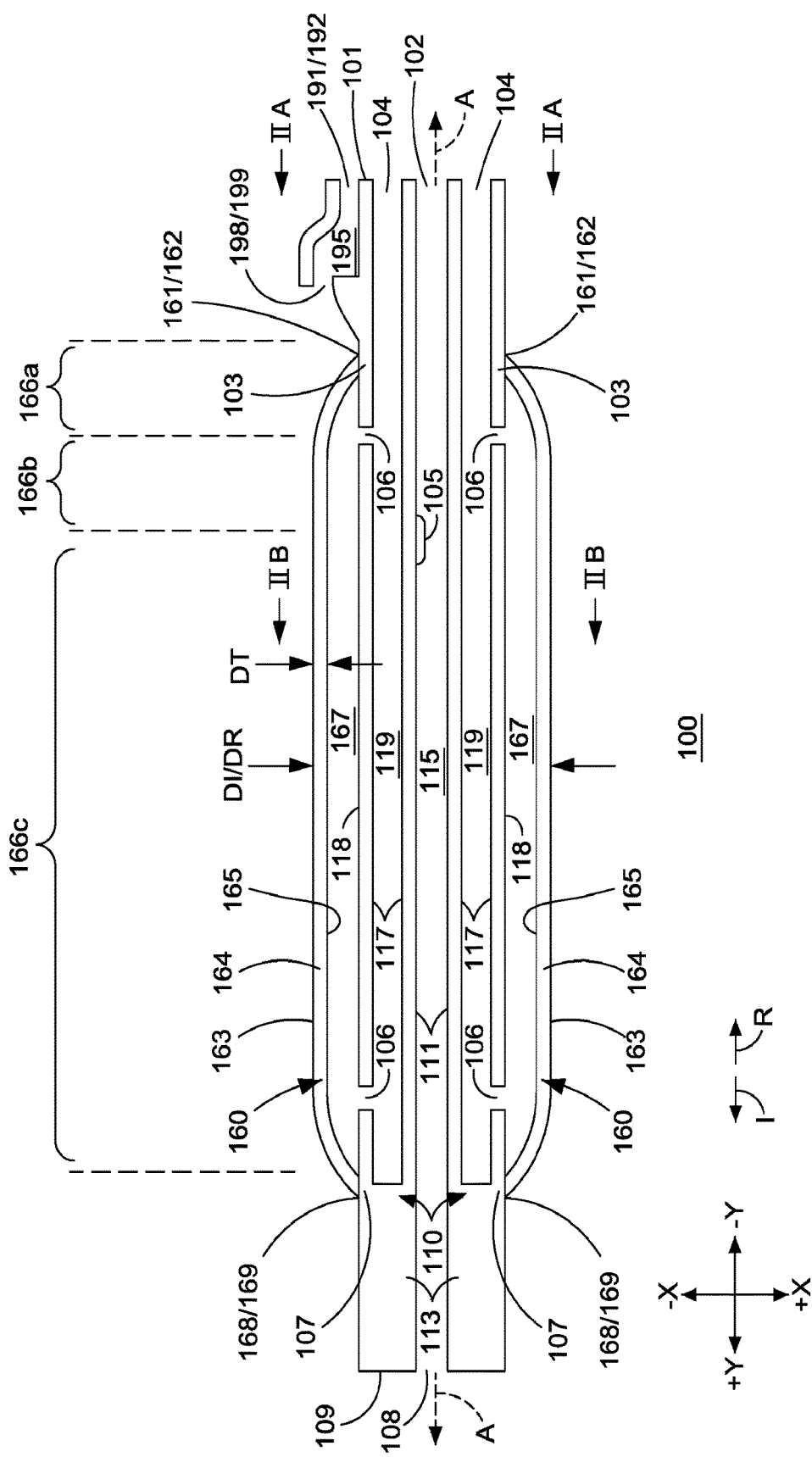
FIG. 2 is a side elevational view of the intubation assembly of FIGS. 1-1D in an insertion state.
Figure 2B:
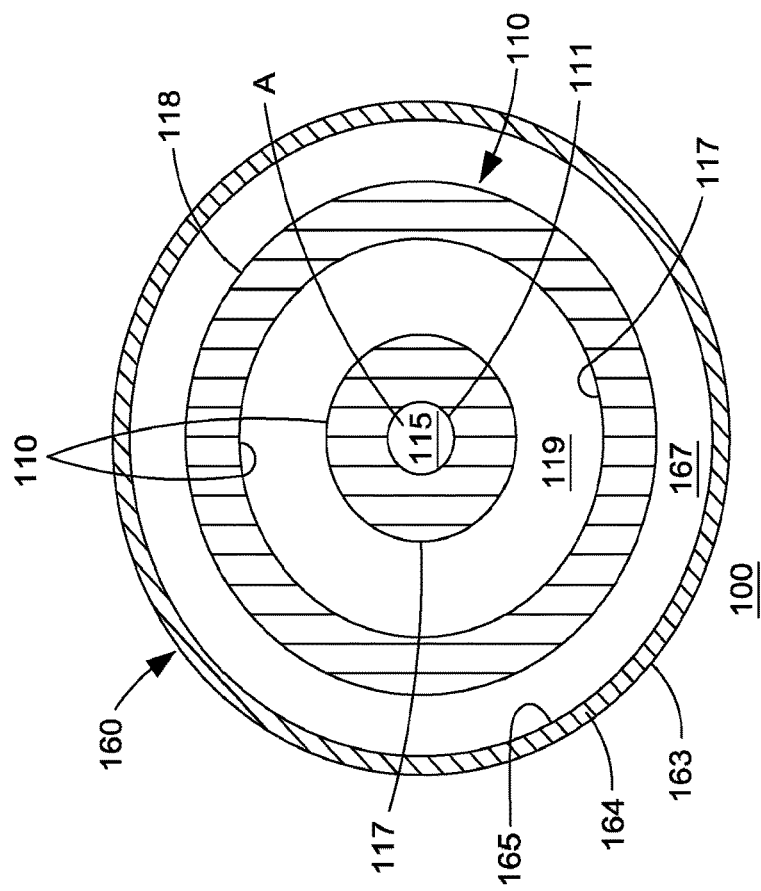
FIG. 2B is a cross-sectional view of the intubation assembly of FIGS. 2 and 2A taken from line IIB-IIB of FIG. 2.
Figure 2A:
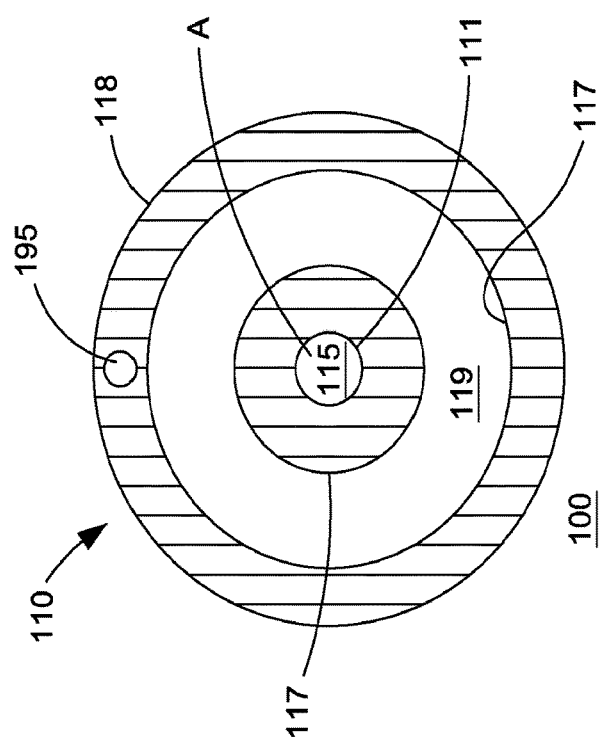
FIG. 2A is a cross-sectional view of the intubation assembly of FIG. 2 taken from line IIA-IIA of FIG. 2.
Figure 3:
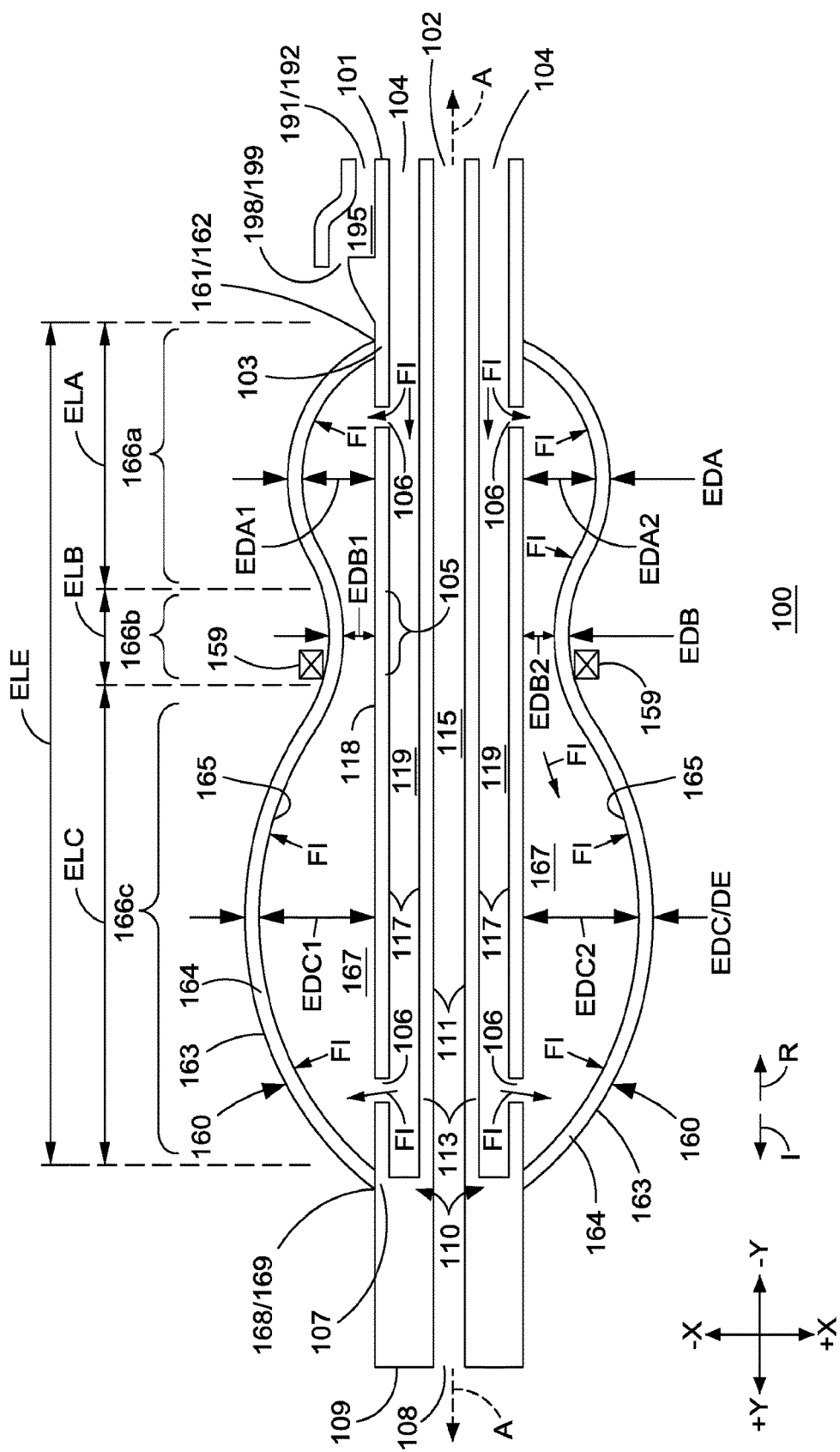
FIG. 3 is a cross-sectional view of the intubation assembly of FIGS. 2-2B in an equilibrium geometry of an expanded state.

As shown in FIGS. 2-7, for example, assembly 100 may include tube subassembly 110 and expander subassembly 160 with such an expander component 164. Tube subassembly 110 may include tube wall(s) 113 that may provide one or more surfaces 111 that may define at least first passageway 115 for extending between at least first tube opening 102 that may provide access to passageway 115 at or near end 101 of assembly 100 and at least one distal or second tube opening 108 that may provide access to passageway 115 at or near end 109 of assembly 100, such that, when assembly 100 is appropriately positioned at least partially within patient 1, material may be injected through opening 102, into and through passageway 115, then out of passageway 115 through opening 108, and into target space 95 of patient 1, and/or such that material may be removed from target space 95, through opening 108, into and through passageway 115, then out of passageway 115 through opening 102 away from patient 1. For example, as shown in FIGS. 2-3, passageway 115 may be a single passageway extending along a longitudinal axis of tube subassembly 110 (e.g., axis A that may extend along an X-axis), although, in other embodiments, passageway 115 may be provided by two or more passageways, at least one of which may at least partially not extend along a longitudinal axis of tube subassembly 110. In some embodiments, opening 102 may not be provided at end 101 of assembly 100 but may instead be provided along and/or through a side surface of tube wall(s) 113 proximal to end 101, and/or opening 108 may not be provided at end 109 of assembly 100 but may instead be provided along and/or through a side surface of tube wall(s) 113 proximal to end 109. Tube wall(s) 113 of subassembly 110 may also provide one or more exterior surfaces 118 of tube subassembly 110 along at least a portion of the length of tube subassembly 110 between ends 101 and 109.

Expander subassembly 160 may include any suitable expander component 164 that may provide exterior surface 163 and interior surface 165 extending between first or proximal expander end 161 and second or distal expander end 169. Expander component 164 may include at least one proximal or first expander opening 162 at or near end 161 and at least one distal or intermediate expander opening 168 at or near end 169. As shown, expander subassembly 160 may be coupled to tube subassembly 110 such that an expander passageway 167 may be provided between interior surface 165 of expander component 164 and exterior surface 118 of tube assembly 110 between ends 161 and 169 of expander component 164. For example, first expander opening 162 may be coupled to and about exterior surface 118 of tube assembly 110 at a first position 103 along the length of tube subassembly 110 using any suitable coupling technique (e.g., adhesive, molding, crimping, etc.) and intermediate expander opening 168 may be coupled to and about exterior surface 118 of tube assembly 110 at a second position 107 along the length of tube subassembly 110 using any suitable coupling technique (e.g., adhesive, molding (e.g., blow molding), crimping, etc.) such that expander passageway 167 may be provided between interior surface 165 of expander component 164 and exterior surface 118 of tube assembly 110 at least partially along the length of expander component 164 between ends 161 and 169. Expander component 164 may be a balloon (e.g., a high volume, low pressure balloon) or any other suitable expander mechanism or component that may be made of any suitable material, such as polyurethane and/or silicone, that may define a space that may be inflatable by air or any other suitable fluid (e.g., gas or liquid or any other suitable substance that may be able to flow into and/or out of the expander mechanism), such that the space may change shape when pressure therein may change.

Tube wall(s) 113 of subassembly 110 may also provide one or more surfaces 117 of tube subassembly 110 that may define at least second passageway 119 for extending between at least one other proximal or third tube opening 104 that may provide access to passageway 119 at or near end 101 of assembly 100 and at least one expander or fourth tube opening 106 that may be operative to fluidly couple passageway 119 of tube subassembly 110 to expander passageway 167 of expander subassembly 160 (e.g., between positions 103 and 107 along the length of subassembly 110). For example, as shown in FIGS. 2-3, passageway 119 may be a single passageway extending concentrically about a longitudinal axis of tube subassembly 110 (e.g., axis A) and/or concentrically about passageway 115, although, in other embodiments, passageway 119 may be provided by two or more passageways. In some embodiments, at least one opening 104 may not be provided at end 101 of assembly 100 but may instead be provided along and/or through a side surface of tube wall(s) 113 proximal to end 101. As shown in FIGS. 2-3, two or more tube openings 106 may be provided through tube wall(s) 113 of tube subassembly 110 (e.g., between surfaces 117 and 118), each of which may be operative to fluidly couple passageway 119 of tube subassembly 110 to expander passageway 167 of expander subassembly 160 (e.g., a first tube opening 106 may be positioned proximate end 161 of expander subassembly 160 while a second tube opening 106 may be positioned proximate end 169 of expander subassembly 160), while, in other embodiments, only a single tube opening 106 may be provided for coupling passageways 119 and 167.

Figure 4:
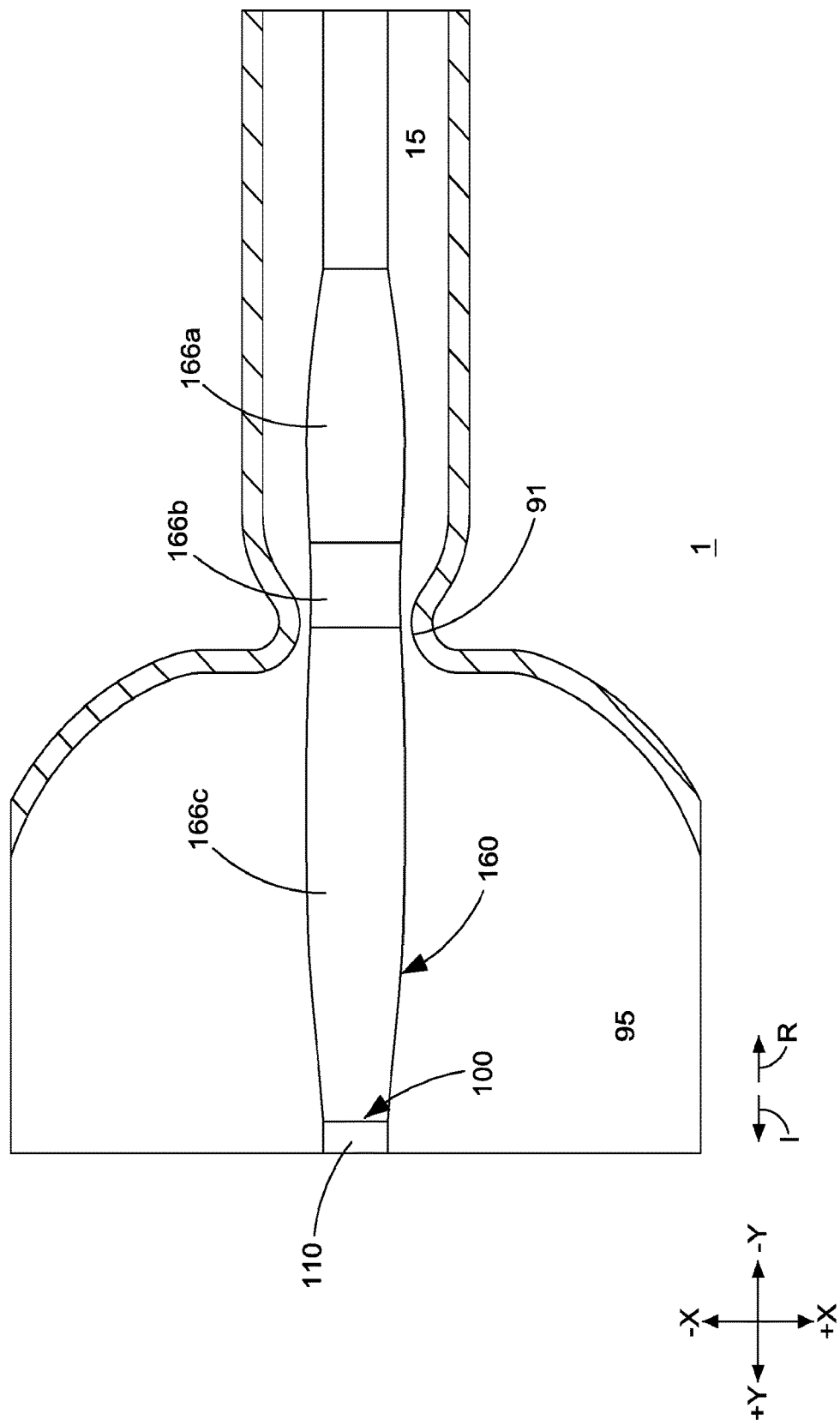
FIG. 4 is a side elevational view of the intubation assembly of FIGS. 2-3 in the insertion state within a patient.
Figure 5:
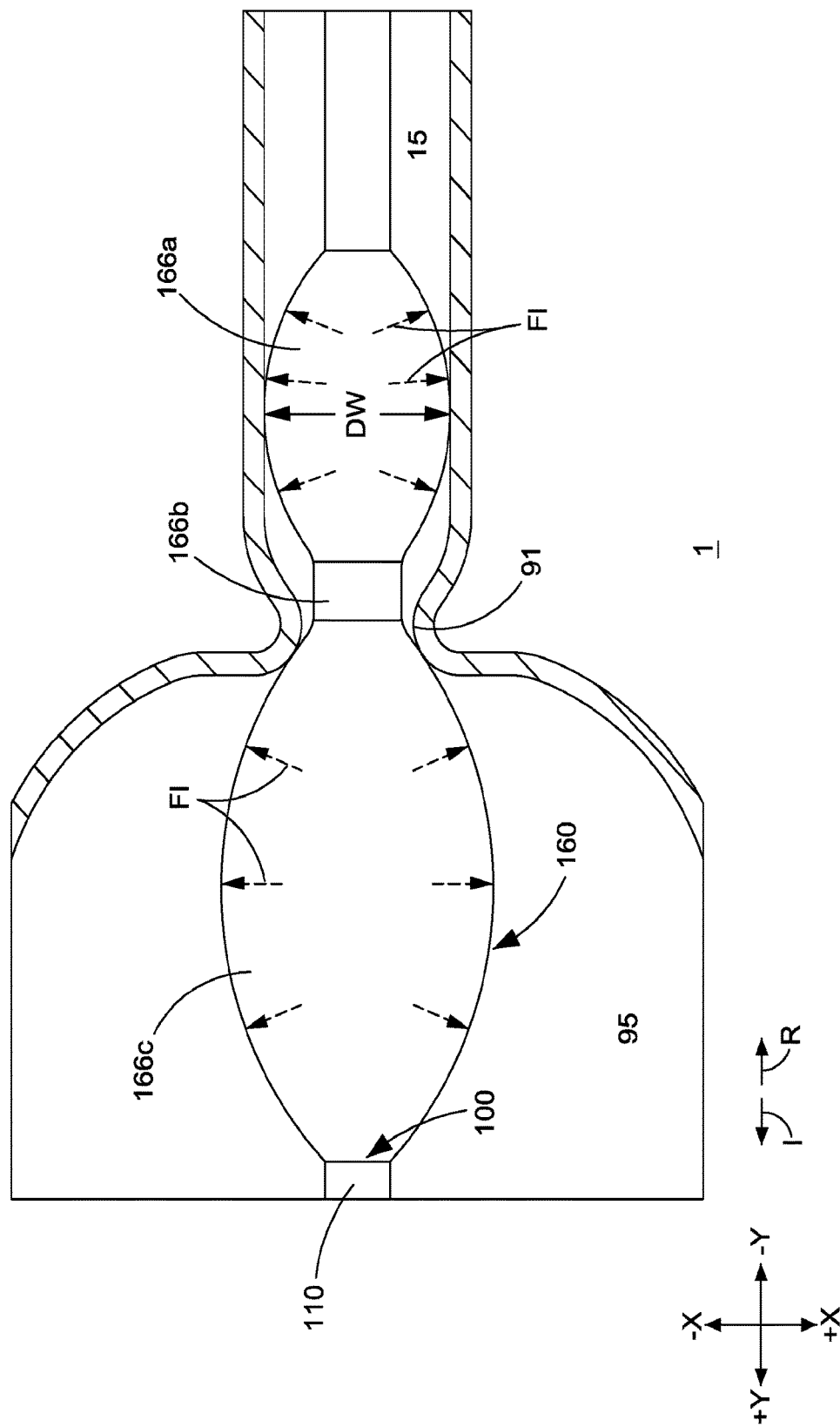
FIG. 5 is a side elevational view of the intubation assembly of FIGS. 2-4 in the equilibrium geometry of the expanded state within a patient.
Figure 6:
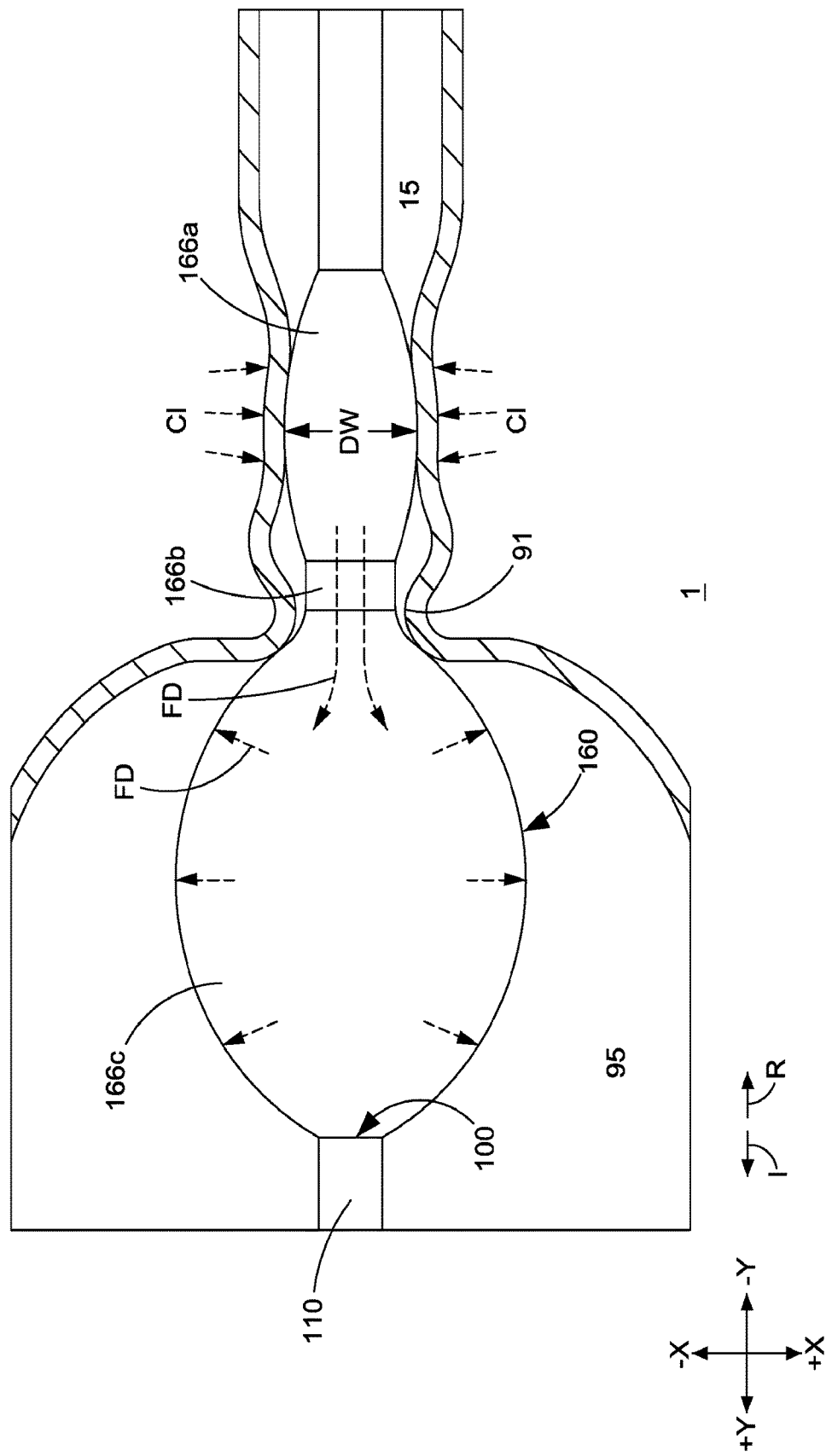
FIG. 6 is a side elevational view of the intubation assembly of FIGS. 2-5 in a deformed geometry of the expanded state within a patient.
Figure 7:
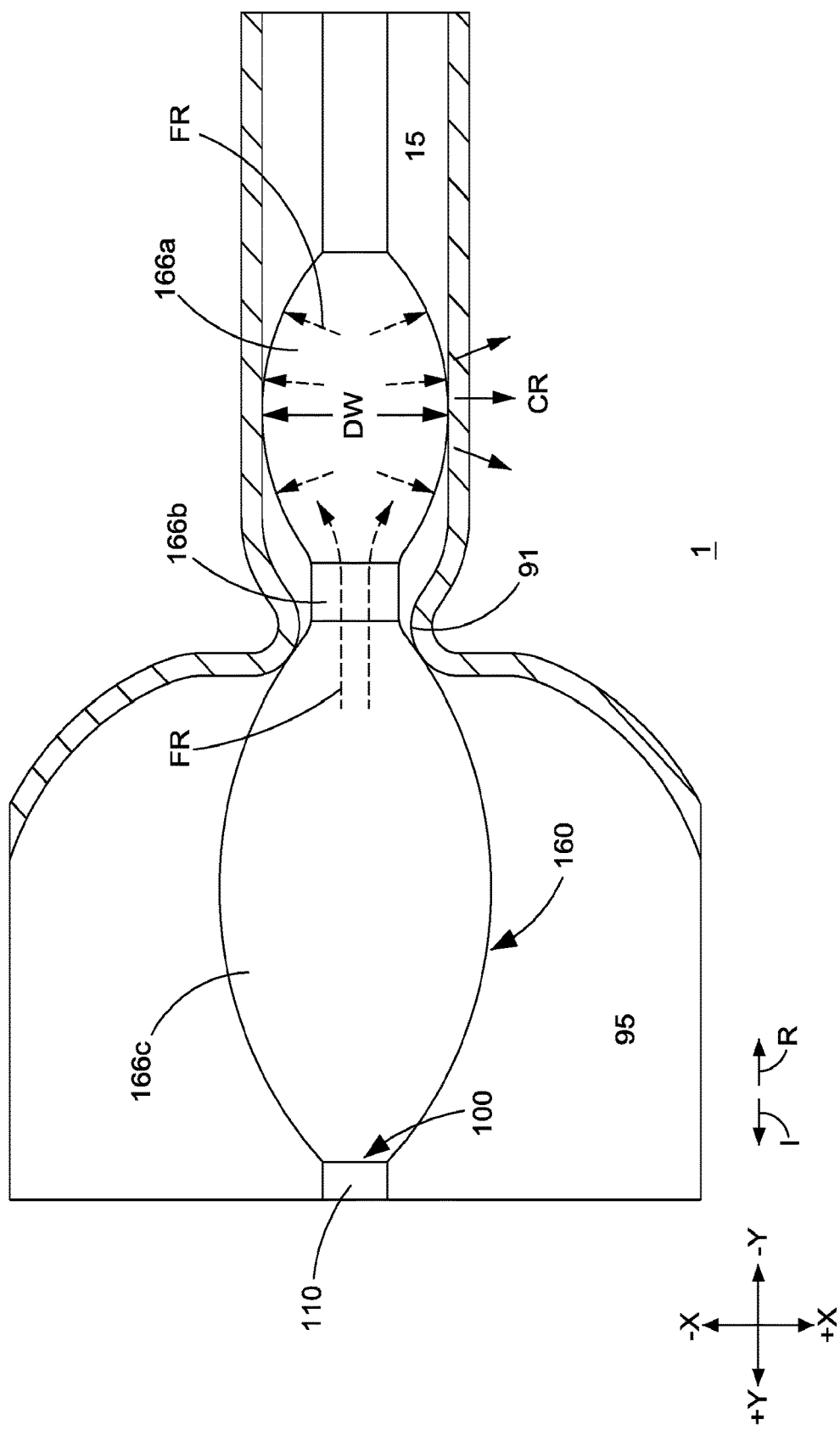
FIG. 7 is a side elevational view of the intubation assembly of FIGS. 2-6 in the equilibrium geometry of the expanded state within a patient.

Any suitable fluid (e.g., air) may be injected (e.g., by operator O using any suitable fluid delivery system (not shown)) through at least one opening 104, into and through passageway 119, then out of passageway 119 through at least one tube opening 106, and then into expander passageway 167 for at least partially inflating expander component 164 about tube subassembly 110 for reconfiguring expander subassembly 160 from a natural or relaxed or un-inflated state (e.g., when no external forces of assembly 100 are being applied to expander component 164 (e.g., as shown in FIGS. 2 and 4)) into an unnatural or tensioned or at least partially inflated state (e.g., when the injected fluid within expander passageway 167 applies forces to expander component 164 (e.g., as shown in FIGS. 3 and 5-7)), which may reconfigure assembly 100 from an insertion state (e.g., as shown in FIGS. 1 and 2 and 4) into an expanded state (e.g., as shown in FIGS. 1A and 3 and 5-7). Additionally or alternatively, any suitable fluid (e.g., air) may be removed (e.g., by operator O using any suitable fluid removal system (not shown)) from expander passageway 167 through at least one tube opening 106, into and through passageway 119, then out of passageway 119 through at least one opening 104 for at least partially deflating expander component 164 about tube subassembly 110 for reconfiguring expander subassembly 160 from an unnatural or tensioned or at least partially inflated state (e.g., when the fluid within expander passageway 167 to be removed applies forces to expander component 164 (e.g., as shown in FIGS. 3 and 5-7)) into a natural or relaxed or un-inflated state (e.g., when no fluid within expander passageway 167 applies force to expander component 164 (e.g., as shown in FIGS. 2 and 4)), which may reconfigure assembly 100 from an expanded state (e.g., as shown in FIGS. 1A and 3 and 5-7) into a removal state (e.g., as shown in FIGS. 1D and 2 and 4). Expander subassembly 160 may be coupled to tube subassembly 110 and configured such that expander subassembly 160 (e.g., expander component 164) may be expanded to an equilibrium geometry of a particular unnatural or tensioned or at least partially inflated state of FIGS. 3 and 5 and 7 when a particular amount (e.g., volume (e.g., a volume of 30 cubic centimeters or 50 cubic centimeters or any other suitable amount)) of fluid is injected into assembly 100 through opening 104 and retained within assembly 100 (e.g., within passageways 119 and 167) but when no external force (e.g., by patient 1) is applied to expander subassembly 160. Such a particular inflated state of expander subassembly 160 may define a structure of any suitable particular equilibrium geometry. For example, as shown in FIGS. 3 and 5 and 7, the particular equilibrium geometry of a particular inflated state of expander subassembly 160 may include a proximal expander component section 166a, an intermediate expander component section 166b, and a distal expander component section 166c, where proximal expander component section 166a may extend between position 103 and a section 105 along a length ELA of tube subassembly 110 with a maximum cross-sectional dimension (e.g., diameter) EDA, where intermediate expander component section 166b may extend along section 105 along a length ELB of tube subassembly 110 with a maximum cross-sectional dimension (e.g., diameter) EDB, and where distal expander component section 166c may extend between section 105 and position 107 along a length ELC of tube subassembly 110 with a maximum cross-sectional dimension (e.g., diameter) EDC. Expander subassembly 160 may be manufactured and/or coupled to tube subassembly 110 and/or inflated in any suitable manner(s) such that the equilibrium geometry of a particular inflated state of expander subassembly 160 may be operative to retain the portion of patient 1 at opening 91 of target space 95 between proximal expander component section 166a and distal expander component section 166c (e.g., along intermediate expander component section 166b) when assembly 100 is in its expanded state and appropriately positioned within patient 1 (see, e.g., FIG. 5). In some embodiments, ELA may be about 3 centimeters and/or ELC may be about 2 centimeters. Expander component section 166a may include a tooth-shape along length ELA, and/or expander component section 166c may be disc shaped to minimize its volume, where EDC may be about 5 centimeters to 6 centimeters while ELC may be about 2 centimeters in the equilibrium expanded state of expander assembly 160. In some embodiments, as shown, the geometry of a particular inflated state of one, some, or each expander component section of expander subassembly 160 may be symmetrical or asymmetrical about longitudinal axis A of tube subassembly 110. For example, a maximum cross-sectional dimension (e.g., diameter) EDA1 of proximal expander component section 166a between a first (e.g., top) side of tube subassembly 110 may be the same as or different than a maximum cross-sectional dimension (e.g., diameter) EDA2 of proximal expander component section 166a between a second (e.g., bottom) side of tube subassembly 110 (e.g., opposite sides with respect to longitudinal axis A), and/or a maximum cross-sectional dimension (e.g., diameter) EDB1 of intermediate expander component section 166b between a first (e.g., top) side of tube subassembly 110 may be the same as or different than a maximum cross-sectional dimension (e.g., diameter) EDB2 of intermediate expander component section 166b between a second (e.g., bottom) side of tube subassembly 110 (e.g., opposite sides with respect to longitudinal axis A), and/or a maximum cross-sectional dimension (e.g., diameter) EDC1 of distal expander component section 166c between a first (e.g., top) side of tube subassembly 110 may be the same as or different than a maximum cross-sectional dimension (e.g., diameter) EDC2 of distal expander component section 166c between a second (e.g., bottom) side of tube subassembly 110 (e.g., opposite sides with respect to longitudinal axis A). In some embodiments, intermediate expander component section 166b may be prevented from expanding beyond a particular cross-sectional dimension of its equilibrium geometry due to the structural composition of expander component 164 (e.g., despite at least a portion of proximal expander component section 166a and/or at least a portion of distal expander component section 166c being able to expand beyond a particular cross-sectional dimension of its equilibrium geometry (see, e.g., an increase in a dimension of distal expander component section 166c between its equilibrium geometry of FIG. 5 and a varied geometry of FIG. 6)). Alternatively, any suitable mechanism 159, such as a rigid band of material, may be positioned about expander component 164 along at least a portion of intermediate expander component section 166b to prevent intermediate expander component section 166b from expanding beyond maximum cross-sectional dimension (e.g., diameter) EDB of the equilibrium geometry of FIGS. 3 and 5 while still allowing a portion of expander passageway 167 to extend between intermediate expander component section 166b if expander component 164 and surface 118 of tube subassembly 110. In an embodiment, the first component section 166a can be separated from or third component section 166c by a non-expanding portion of the tube wall (2200 as shown in FIGS. 22A-22D).

When assembly 100 is in an insertion state (see, e.g., FIGS. 1, 2, and 4, where expander subassembly 160 may be in a natural or relaxed or un-inflated state such that maximum cross-sectional dimension (e.g., diameter) DI of expander subassembly 160 (e.g., of at least distal expander component section 166c) may be less than cross-sectional dimension (e.g., diameter) DO of opening 91 of patient 1), assembly 100 may be inserted (e.g., in the direction of arrow I) into patient 1 to a particular position (e.g., a position at which at least a portion of distal expander component section 166c may be positioned within target space 95 of patient 1 and a position at which at least a portion of proximal expander component section 166a may be positioned within passageway 15 of patient 1 and/or a position at which at least a portion of intermediate expander component section 166b may be positioned within or proximate opening 91 of patient 1), as shown in FIG. 4. Then, assembly 100 may be re-configured into an expanded state (see, e.g., FIGS. 1A, 3, and 5, where expander subassembly 160 may be in a particular unnatural or tensioned or at least partially inflated state such that maximum cross-sectional dimension (e.g., diameter) DE of expander subassembly 160 (e.g., at least dimension EDC of distal expander component section 166c) may be greater than cross-sectional dimension (e.g., diameter) DO of opening 91 of patient 1) within patient 1, as shown in FIG. 5 (e.g., when a particular amount (e.g., volume) of fluid is injected (e.g., by operator O in the direction of arrows FI of FIGS. 3 and 5) into assembly 100 through opening 104 and retained within assembly 100 (e.g., within passageways 119 and 167) but when no external force (e.g., by patient 1) is applied to expander subassembly 160). As shown in FIGS. 3 and 5, when assembly 100 is in its expanded state, at least a portion of expander subassembly 160 may have a cross-sectional dimension (e.g., at least a portion of distal expander component section 166c may have a cross-sectional dimension) that may be at least equal to or greater than dimension DO of opening 91 of patient 1, such that at least a portion of surface 163 of expander component 164 of expander subassembly 160 may contact or otherwise interact with at least a portion of wall 93 of target 95 for safely securing at least a portion of expanded assembly 100 at a particular position within patient 1 (e.g., for securing at least a portion of distal expander component section 166c within target 95 and preventing that portion from passing in the direction of arrow R through opening 91 and into passageway 15) and/or for safely preventing certain material from traveling between surface 163 of expander component 164 and at least a portion of wall 93 of target 95 and/or at least a portion of wall 13 of passageway 15 (e.g., such that movement of any material between target space 95 and passageway 15 about the exterior of assembly 100 in its expanded state may be limited or prevented). Additionally or alternatively, as shown in FIGS. 3 and 5, when assembly 100 is in its expanded state, at least a portion of expander subassembly 160 may have a cross-sectional dimension (e.g., at least a portion of proximal expander component section 166a may have a cross-sectional dimension) that may be at least equal to or greater than dimension DO of opening 19 of patient 1, such that at least a portion of surface 163 of expander component 164 of expander subassembly 160 may contact or otherwise interact with at least a portion of wall 13 of passageway 15 for safely securing at least a portion of expanded assembly 100 at a particular position within patient 1 (e.g., for securing at least a portion of proximal expander component section 166a within passageway 95 and preventing that portion from passing in the direction of arrow I through opening 19 and into target space 95) and/or for safely preventing certain material from traveling between surface 163 of expander component 164 and at least a portion of wall 93 of target 95 and/or at least a portion of wall 13 of passageway 15 (e.g., such that movement of any material between target space 95 and passageway 15 about the exterior of assembly 100 in its expanded state may be limited or prevented). In some embodiments, the maximum cross-sectional dimension (e.g., diameter) EDC of distal expander component section 166c may be larger than maximum cross-sectional dimension (e.g., diameter) EDA of proximal expander component section 166a in a particular inflated state (e.g., the state of FIGS. 3 and 5) and/or the maximum cross-sectional dimension of each one of distal expander component section 166c and first component section 166a may be larger than the maximum cross-sectional dimension EDB of intermediate expander component section 166b (e.g., to match the sizes of target space 95, opening 91, and passageway 15 within which respective expander components 166c, 166b, and 166a may be positioned in the functional position of expanded assembly 100 of FIG. 5. When in the functional position of FIG. 5, material may be passed through expanded subassembly 100 (e.g., through passageway 115 of tube subassembly 110) between target space 95 and passageway 15, either in the direction of arrow I or in the direction of arrow R.

Although the amount (e.g., volume) of fluid that may be injected into and then held within expander passageway 167 of assembly 100 when assembly 100 is in the particular expanded state of FIGS. 3 and 5 may be fixed or predetermined, a dimension of at least a portion of patient 1 may vary during use of assembly 100 in that state. For example, cross-sectional dimension DW of passageway 15 may expand and/or contract while assembly 100 is positioned within patient 1, such as due to patient 1 swallowing. Assembly 100 may be configured to alter its geometry in conjunction with such variation of patient 1 so that assembly 100 may maintain its ability to maintain the position of assembly 100 within patient 1 (e.g., to maintain at least a portion of expander component 160 within target space 95 and to maintain at least a portion of expander component 160 within passageway 15). For example, as shown between FIGS. 5 and 6, expander subassembly 160 may be configured such that, in a particular inflated state (e.g., of FIGS. 3 and 5-7 (e.g., with a fixed particular amount of fluid within passageway 167)), when walls of patient 1 may contract or squeeze against expander subassembly 160 or otherwise reduce the cross-sectional dimension DW or any other suitable cross-sectional dimension of passageway 15 (e.g., in the direction of arrows CI of FIG. 6), proximal expander component section 166a may be operative to at least partially or fully deflate by passing fluid from within a portion of passageway 167 of proximal expander component section 166a to within a portion of passageway 167 of distal expander component section 166c (e.g., in the direction of arrows FD of FIG. 6 (e.g., via a portion of passageway 167 of intermediate expander component section 166b and/or via passageway 119 and two or more different openings 106)), thereby further inflating distal expander component section 166c (e.g., increasing its inflated volume, which may increase its cross-sectional dimension EDC and/or its length ELC). Therefore, while expander subassembly 160 may be configured to have an equilibrium geometry of FIGS. 3 and 5 when a particular amount of fluid is held within expander passageway 167 for a particular expanded state of assembly 100 (e.g., when no external forces are applied to assembly 100 (e.g., by patient 1)), expander subassembly 160 may also be configured to adjust its geometry (e.g., from the equilibrium geometry of FIG. 5 to an adjusted geometry of FIG. 6) when the amount of fluid held within expander passageway 167 remains the same but when an external force is applied to assembly 100 (e.g., by contraction forces in the direction of arrows CI by patient 1) and may force fluid from one portion of passageway 167 to another portion of passageway 167 (e.g., by forcing fluid to pass from within a portion of passageway 167 of proximal expander component section 166a to within a portion of passageway 167 of distal expander component section 166c (e.g., in the direction of arrows FD of FIG. 6)). Such an adjustment of the geometry of a particular expanded state of assembly 100 between that of FIG. 5 and that of FIG. 6 may maintain a relationship between assembly 100 and patient 1 for maintaining assembly 100 at the functional position within patient 1 (e.g., maintain a larger cross-sectional dimension of distal expander component section 166c within target space 95 than that of opening 91 to prevent end 109 of assembly 100 from being inadvertently removed from target space 95). Therefore, in some embodiments, a particular equilibrium geometry of a particular inflated state of expander subassembly 160 (e.g., of FIG. 5) may be configured such that some or even all of the volume of fluid within proximal expander component section 166a in that equilibrium geometry may be transferred to and held within distal expander component section 166c when in a deformed geometry of that particular inflated state (e.g., of FIG. 6) without popping or otherwise rupturing distal expander component section 166c or any other portion of expander subassembly 160 (e.g., the volume of fluid within proximal expander component section 166a in the equilibrium geometry combined with the volume of fluid within distal expander component section 166c in the equilibrium geometry may together be held within distal expander component section 166c in the deformed geometry without damaging expander subassembly 160). In an embodiment, a burst valve can be attached to the proximate opening 104 in order to release excess pressure. Therefore, distal expander component section 166c may not be fully expanded in its equilibrium geometry but may instead be configured to expand further (e.g., to be filled with more fluid to expand to a greater deformed geometry), while proximal expander component section 166a may or may not be fully expanded in its equilibrium geometry (e.g., proximal expander component section 166a may not be able to take on much more fluid than the amount within proximal expander component section 166a in its equilibrium geometry).

Additionally or alternatively, as shown between FIGS. 6 and 7, expander subassembly 160 may be configured such that, in a particular inflated state (e.g., of FIGS. 3 and 5-7 (e.g., with a fixed particular amount of fluid within passageway 167)), when walls of patient 1 may expand away from expander subassembly 160 or otherwise increase the cross-sectional dimension DW or any other suitable cross-sectional dimension of passageway 15 (e.g., in the direction of arrows CR of FIG. 7), proximal expander component section 166a may be operative to at least partially inflate by receiving fluid from within a portion of passageway 167 of distal expander component section 166c to within a portion of passageway 167 of proximal expander component section 166a (e.g., in the direction of arrows FR of FIG. 7 (e.g., via a portion of passageway 167 of intermediate expander component section 166b and/or via passageway 119 and two or more different openings 106)), thereby re-inflating proximal expander component section 166a and increasing its cross-sectional dimension EDA back to that of the equilibrium of assembly 100 of FIGS. 3 and 5. Therefore, while expander subassembly 160 may be configured to have an equilibrium geometry of FIGS. 3 and 5 and 7 when a particular amount of fluid is held within expander passageway 167 for a particular expanded state of assembly 100 (e.g., when no external forces are applied to assembly 100 (e.g., by patient 1)), expander subassembly 160 may also be configured to adjust its geometry (e.g., from the adjusted geometry of FIG. 6 back to an equilibrium geometry of FIG. 7) when the amount of fluid held within expander passageway 167 remains the same but when an external force is removed from assembly 100 (e.g., when expansion forces in the direction of arrows CR by patient 1 remove a force on assembly 100 by patient 1) and may force fluid from one portion of passageway 167 to another portion of passageway 167 (e.g., by forcing fluid to pass from within a portion of passageway 167 of distal expander component section 166c to within a portion of passageway 167 of proximal expander component section 166a (e.g., in the direction of arrows FR of FIG. 7)). Such an adjustment of the geometry of a particular expanded state of assembly 100 between that of FIG. 6 and that of FIG. 7 may maintain a relationship between assembly 100 and patient 1 for maintaining assembly 100 at the functional position within patient 1 (e.g., maintain a larger cross-sectional dimension of distal expander component section 166c within target space 95 than that of opening 91 to prevent end 109 of assembly 100 from being inadvertently removed from target space 95). Such expansion and contraction of dimension DW of patient 1 may be due to peristalsis of the esophagus or any other suitable portion of patient 1 that may routinely occur during any suitable procedure using assembly 100. By configuring at least a portion of expander subassembly 160 to deflect inwardly and rebound outwardly in tandem with expansion and contraction forces of opposing walls of patient 1 about expander subassembly 160 may enable expander subassembly 160 to safely interact with patient 1 during use of assembly 100. In some embodiments, the volume of proximal expander component section 166a may be the same as or less than the volume of distal expander component section 166c when assembly 100 is in its equilibrium geometry of a particular expanded state (e.g., of FIGS. 3, 5, and 7). In some particular embodiments, assembly 100 may be configured such that the volume of proximal expander component section 166a may be less than the volume of distal expander component section 166c when assembly 100 is in its equilibrium geometry of a particular expanded state. Additionally or alternatively, assembly 100 may be configured such that the entirety of, or substantially the entirety of, or at least half of, or less than half of but at least some of the volume of fluid within the portion of expander passageway 167 of proximal expander component section 166a when assembly 100 is in its equilibrium geometry of a particular expanded state may be transferred to within the portion of expander passageway 167 of distal expander component section 166c when the equilibrium geometry of the particular expanded state is deformed to a deformed geometry of the particular expanded state (e.g., the deformed geometry of FIG. 6 (e.g., when an external force is applied to expander component 164 (e.g., by patient 1))) without expander subassembly 160 being damaged (e.g., popping or rupturing or deforming such that it cannot return to its equilibrium geometry when external forces are removed). Therefore, at least some or all of the fluid within the portion of expander passageway 167 of proximal expander component section 166a when assembly 100 is in its equilibrium geometry of a particular expanded state may safely be combined with all of the fluid within the portion of expander passageway 167 of distal expander component section 166c when assembly 100 is in its equilibrium geometry of the particular expanded state and held within the portion of expander passageway 167 of distal expander component section 166c when assembly 100 is in a deformed geometry of the particular expanded state. In some embodiments, expander subassembly 160 may be inflated to its equilibrium expanded state of FIG. 5 yet with each one of component sections 166a, 166b, and 166c positioned at least partially within target space 95 and then assembly 100 may be pulled in the direction of arrow R such that expander subassembly 160 may be positioned with respect to patient 1 as shown in FIG. 5 (e.g., such movement of assembly 100 from an equilibrium expanded state of subassembly 160 within target space 95 to an equilibrium expanded state of subassembly 160 with first component section 166a outside of target space 95 but in passageway 15 may involve expander subassembly 160 deforming to a deformed expanded state while first component section 166a passes through opening 91 (e.g., similar to the deformation between FIGS. 5, 6, and 7)).

Figure 8:
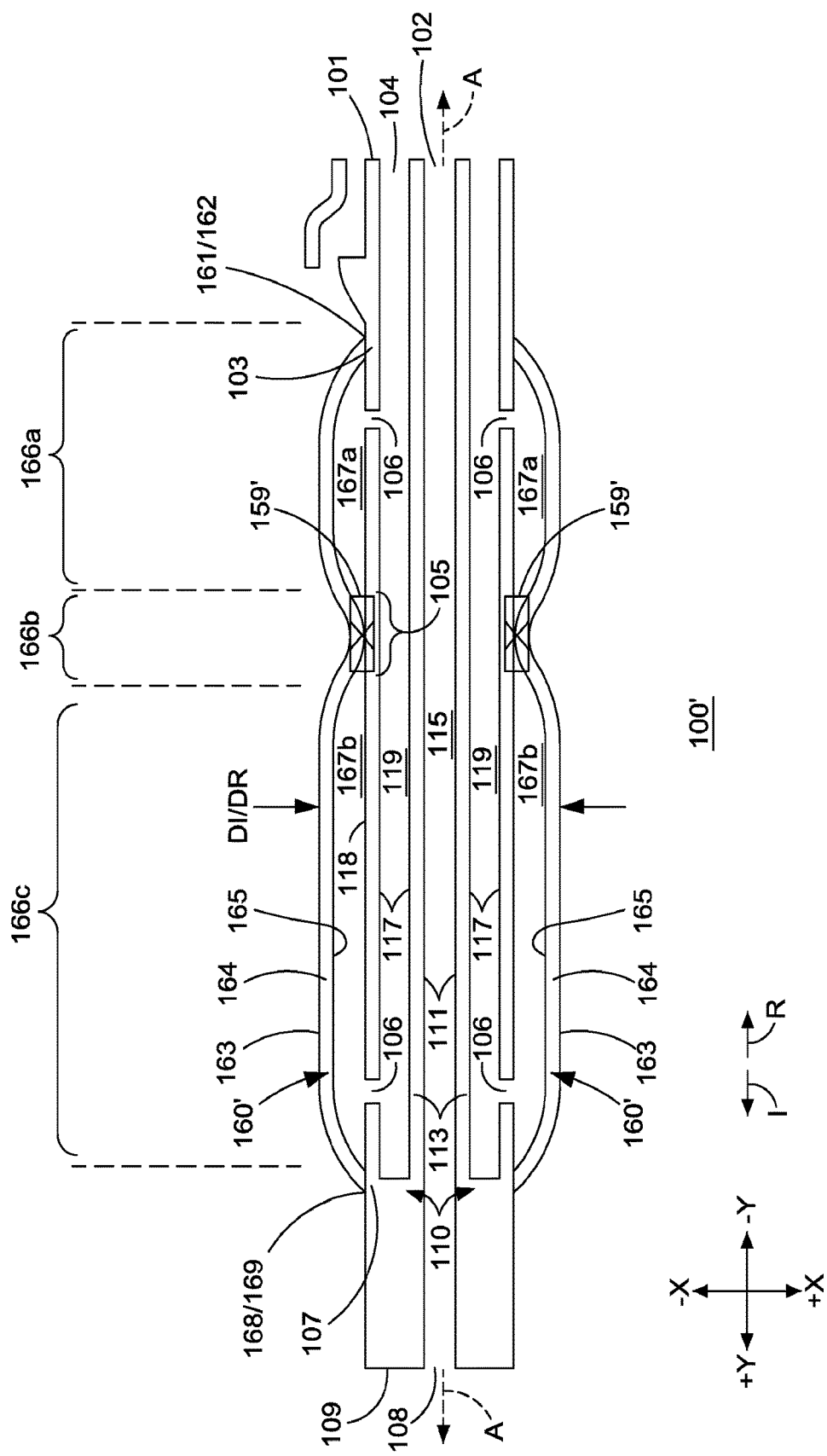
FIG. 8 is a side elevational view of another intubation assembly in an insertion state.
Figure 9:
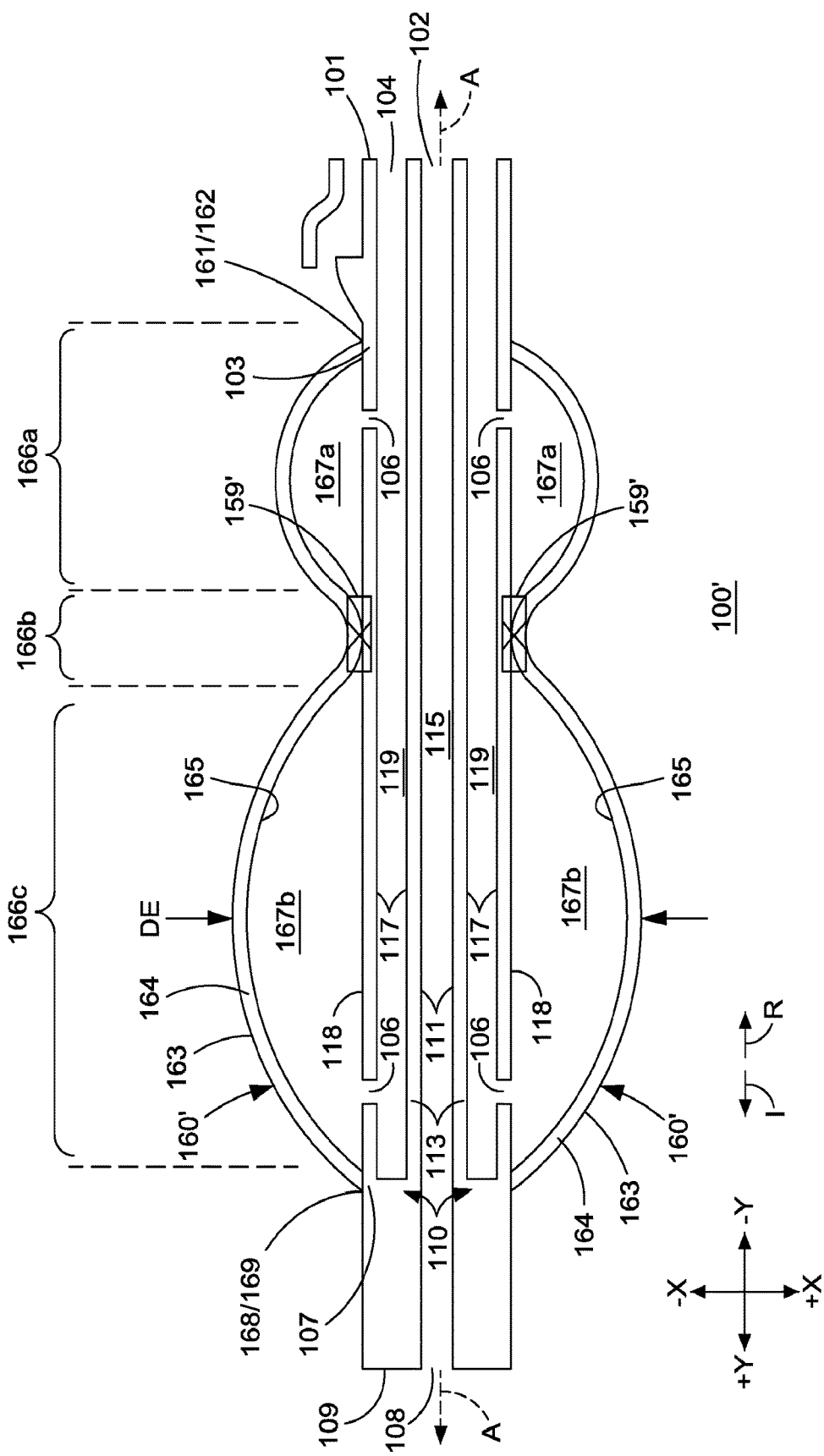
FIG. 9 is a cross-sectional view of the intubation assembly of FIG. 8 in an equilibrium geometry of an expanded state.
Figure 10:
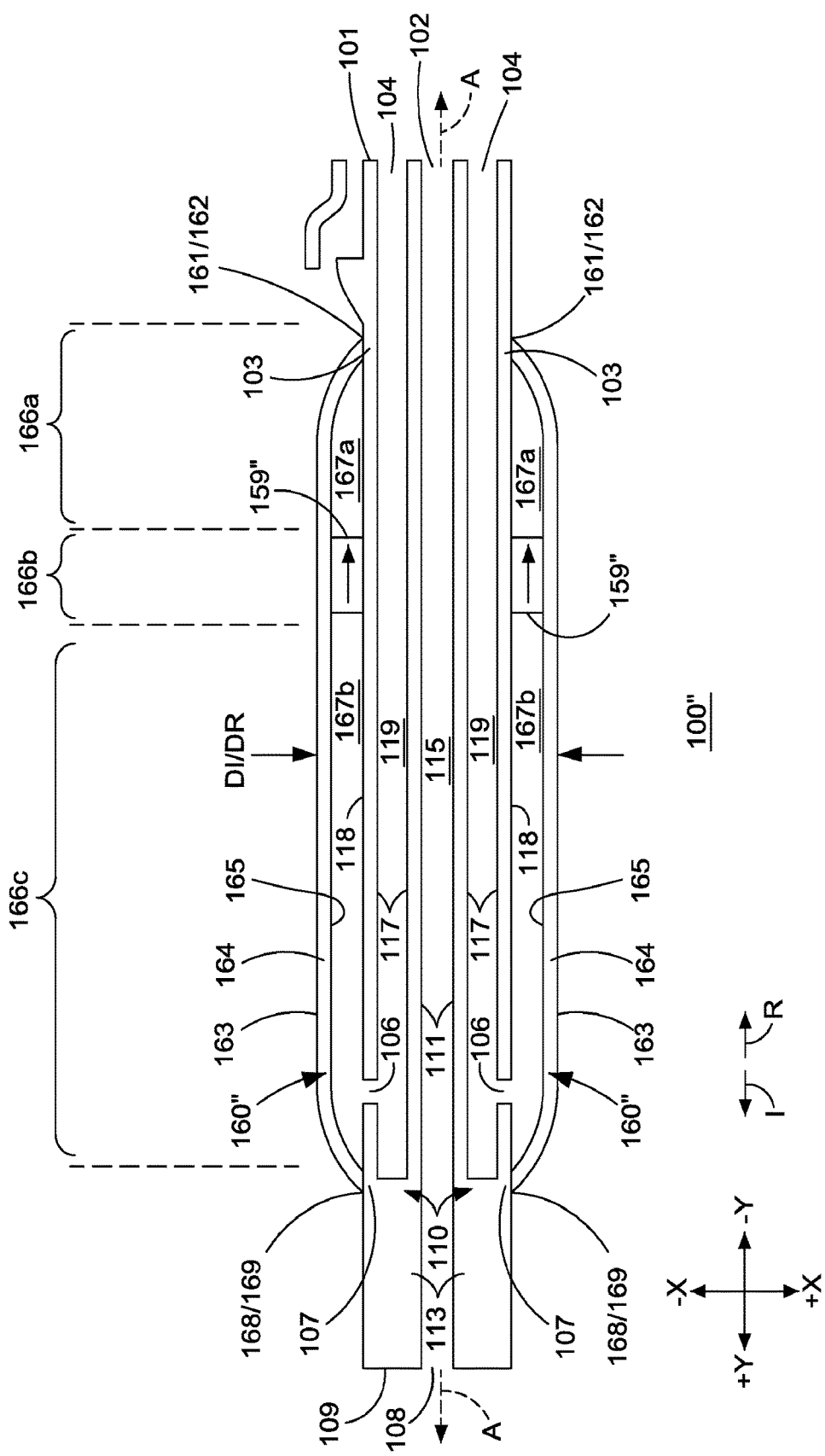
FIG. 10 is a side elevational view of yet another intubation assembly in an insertion state.
Figure 11:
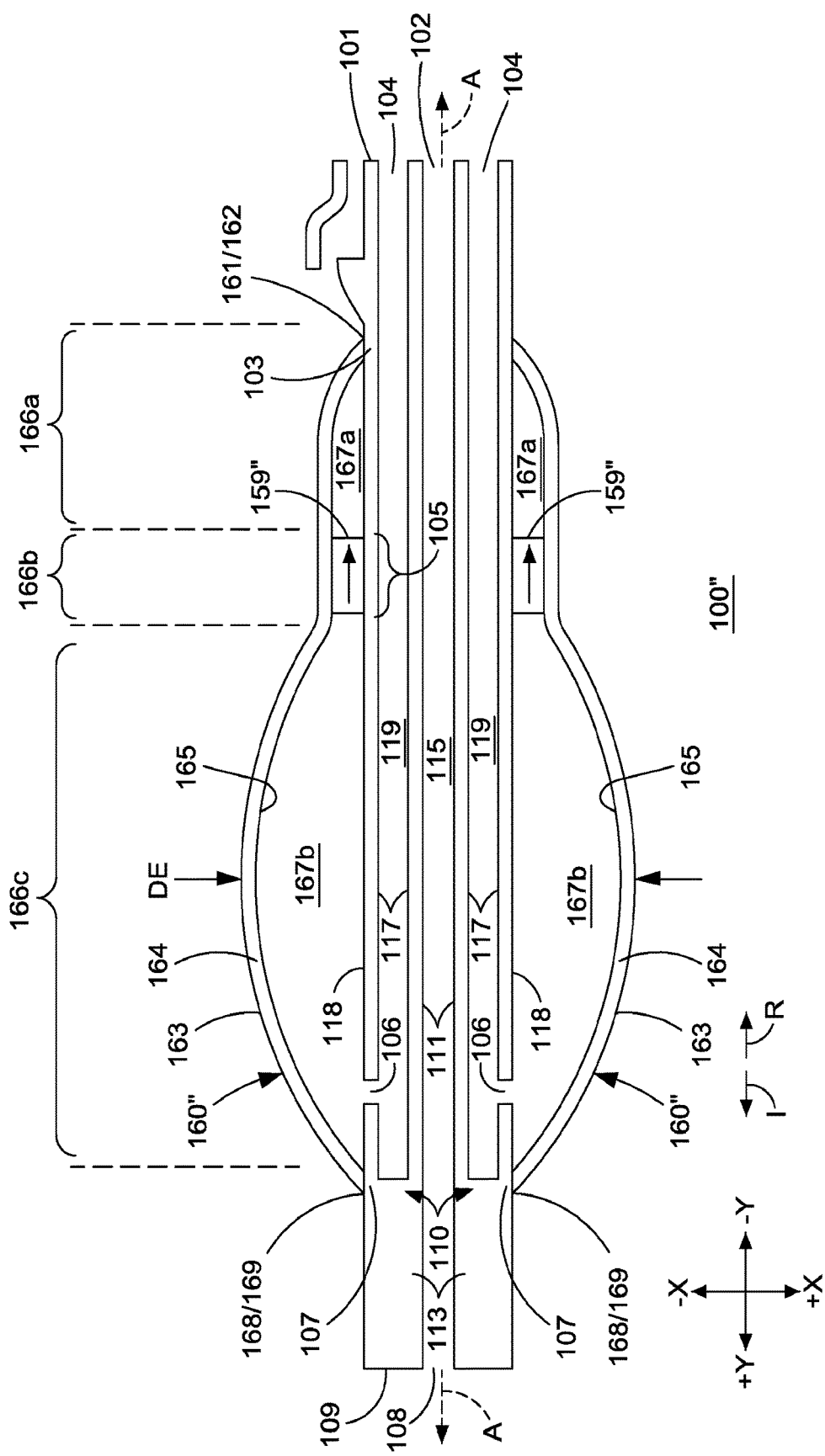
FIG. 11 is a cross-sectional view of the intubation assembly of FIG. 10 in an equilibrium geometry of an expanded state.
Figure 12:
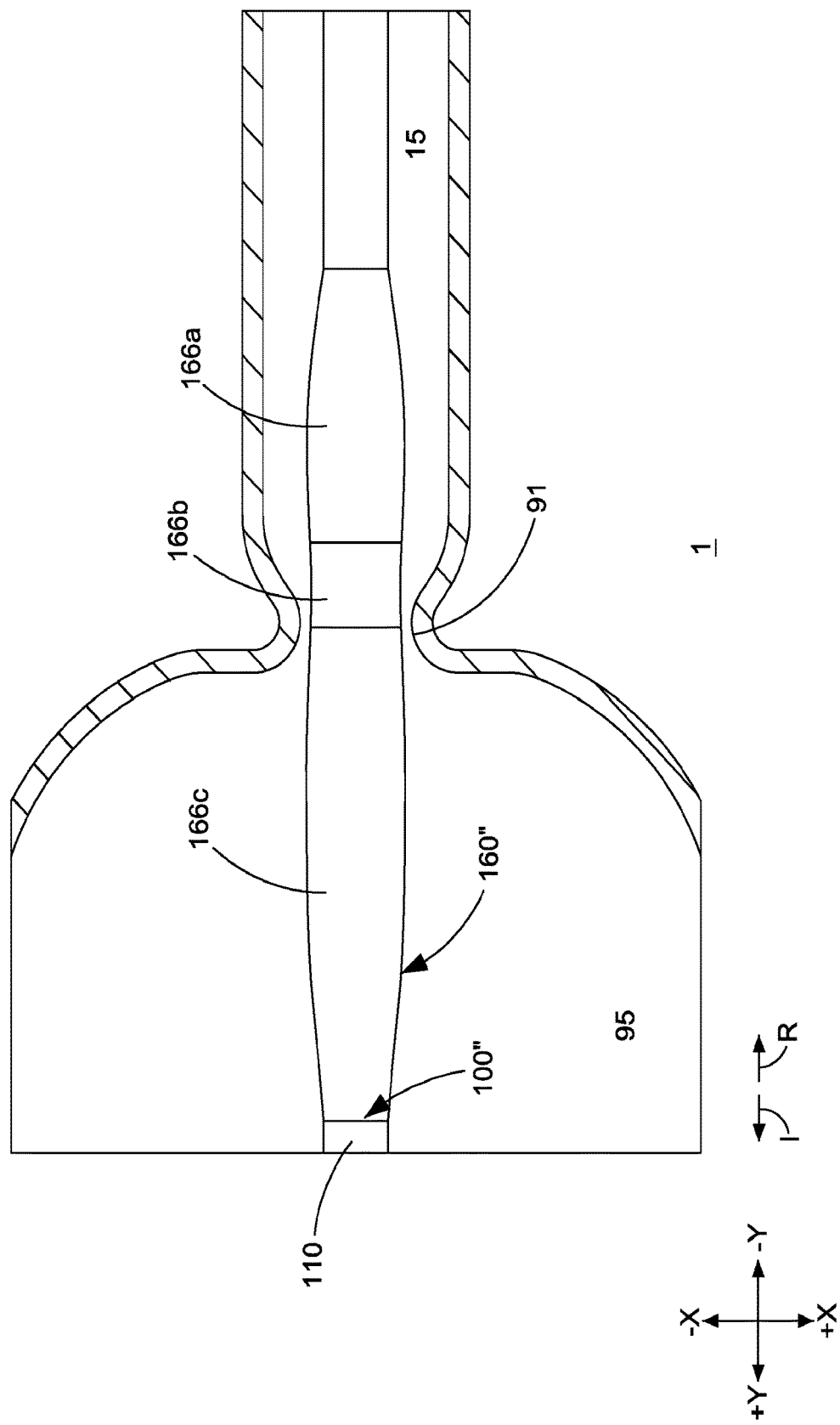
FIG. 12 is a side elevational view of the intubation assembly of FIGS. 10 and 11 in the insertion state within a patient.
Figure 13:
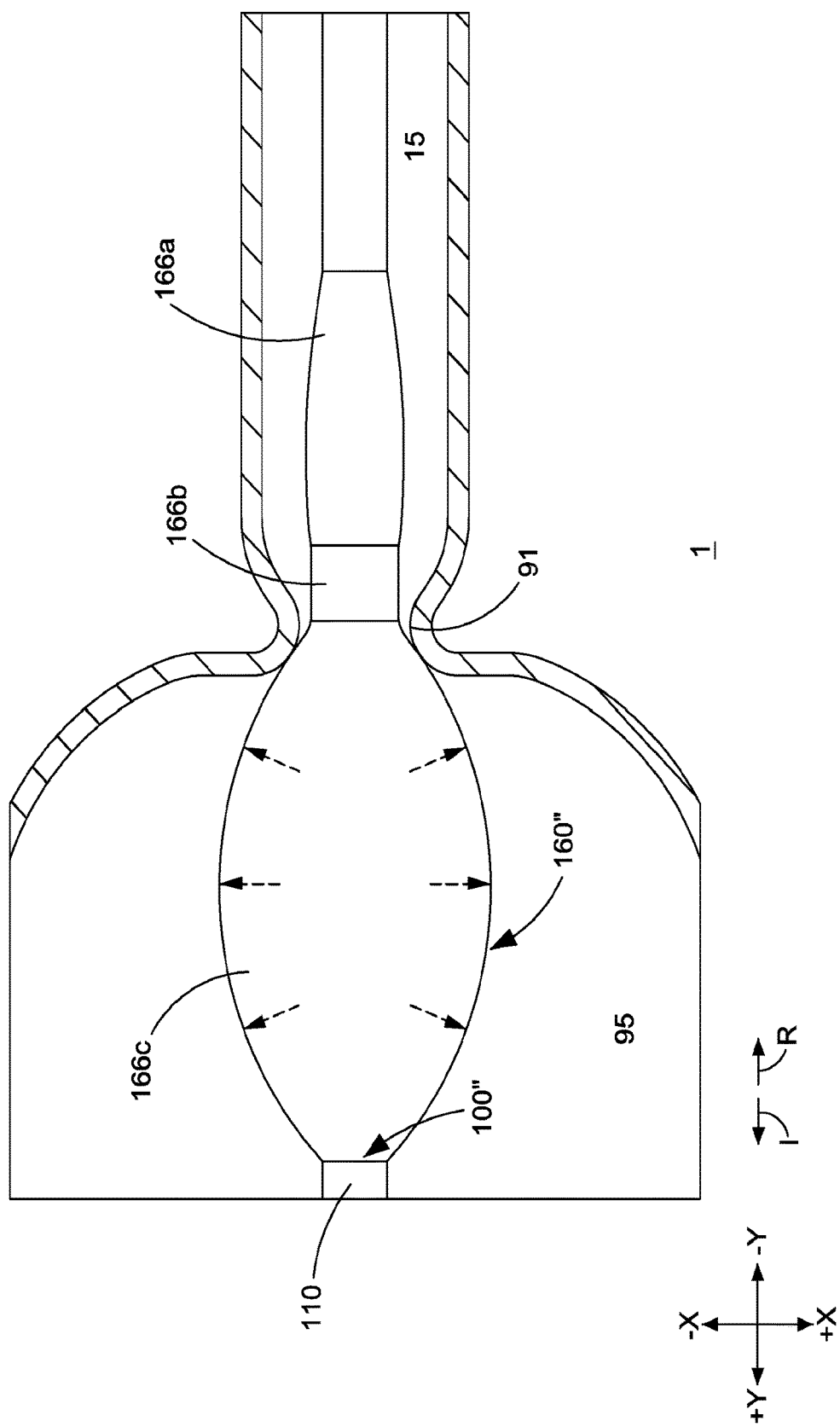
FIG. 13 is a side elevational view of the intubation assembly of FIGS. 10-12 in the equilibrium geometry of the expanded state within a patient.
Figure 14:
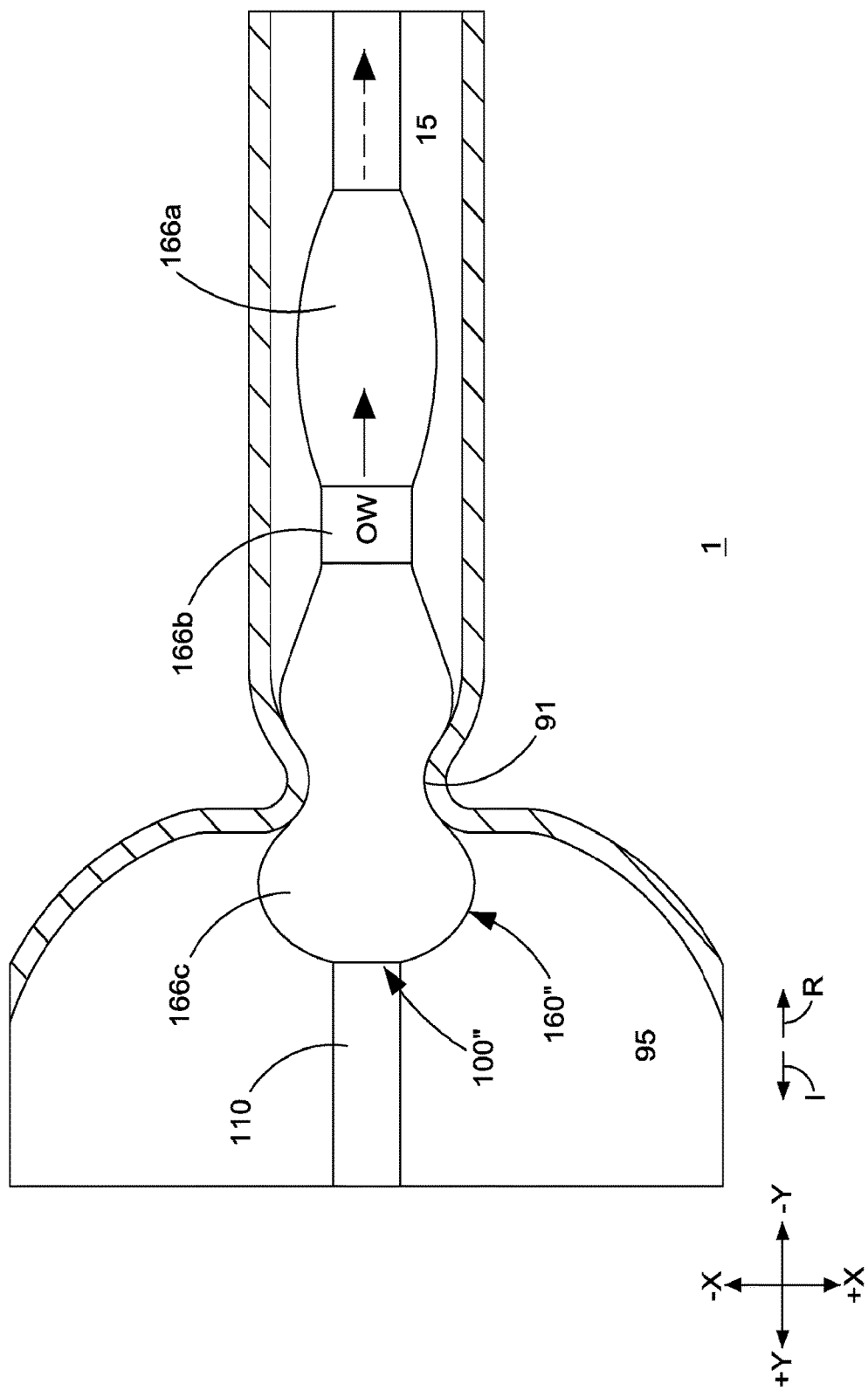
FIG. 14 is a side elevational view of the intubation assembly of FIGS. 10-13 in a first deformed geometry of the expanded state within a patient.
Figure 15:
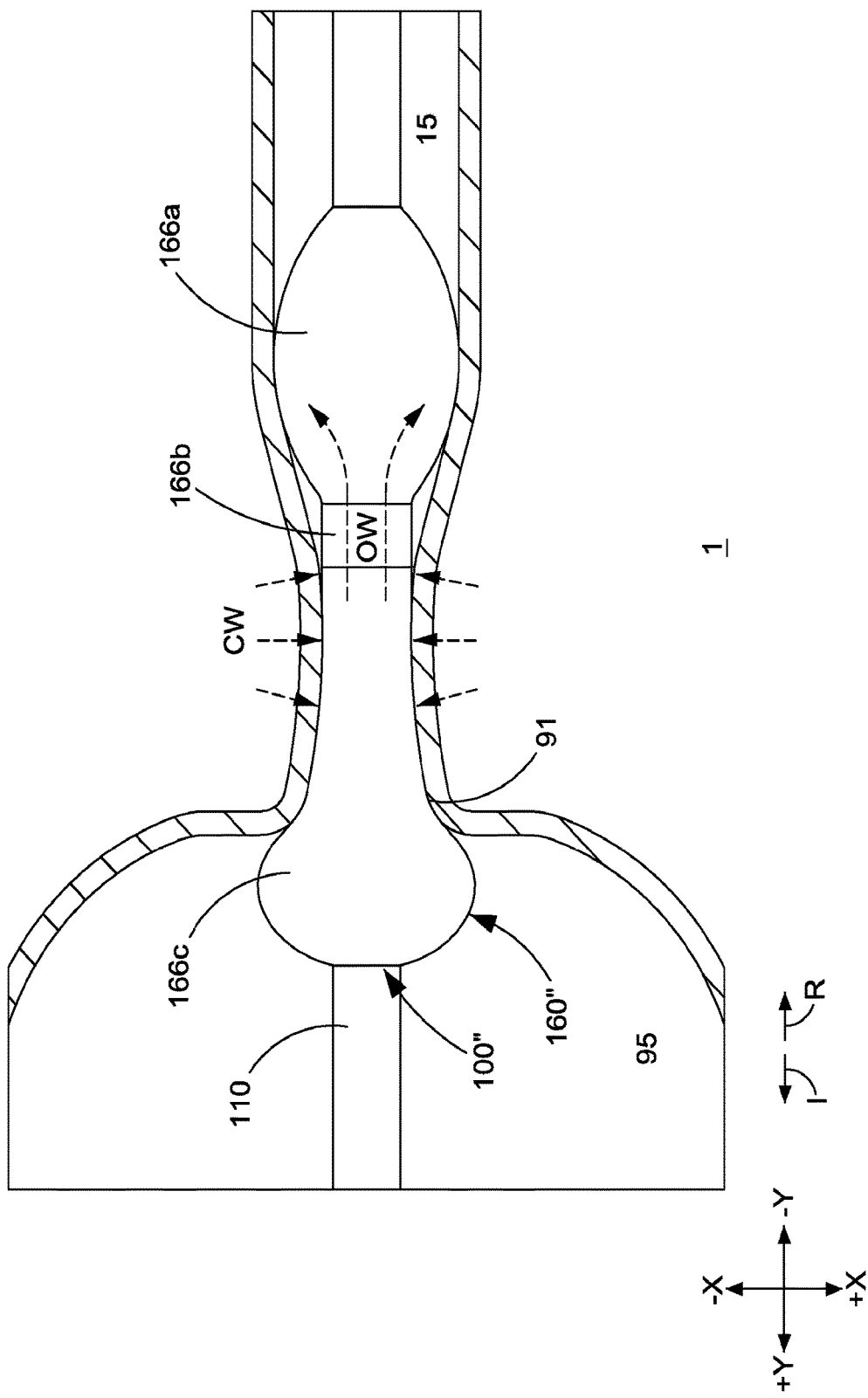
FIG. 15 is a side elevational view of the intubation assembly of FIGS. 10-14 in a second deformed geometry of the expanded state within a patient.

As mentioned, intermediate expander component section 166b of assembly 100 of FIGS. 2-7 may be prevented from expanding at all or at least beyond a particular dimension of its equilibrium geometry due to the structural composition of expander component 164 and/or due to any suitable limiting mechanism 159 of assembly 100. Alternatively, as shown in FIGS. 8 and 9, an expander subassembly 160' of an assembly 100', which may otherwise be similar to assembly 100 of FIGS. 2-7, may include any suitable limiting mechanism 159' (e.g., adhesive, molding (e.g., blow molding), crimping, etc.)) that may physically couple (e.g., seal) a portion of expander component 164 (e.g., at least a portion or the entirety of intermediate expander component section 166b) to a portion of section 105 along tube subassembly 110, which may split expander passageway 167 into at least two distinct expander sub-passageways 167a and 167b that may be fluidly coupled via two or more openings 106 and passageway 119 but not via another sub-passageway of passageway 167. Alternatively, one or more elements of limiting mechanism 159' may be operative to secure ends of two distinct expander components 164 to a portion of section 105 along tube subassembly 110 (e.g., passageway 167a may be defined by a proximal expander component and passageway 167b may be defined by an intermediate expander component that may be distinct from the proximal expander component (e.g., two distinct balloons may be coupled to and about and along different portions of tube subassembly 110)). Alternatively, as shown in FIGS. 10-15, an expander subassembly 160" of an assembly 100", which may otherwise be similar to assembly 100 of FIGS. 2-7, may include any suitable limiting mechanism 159", such as a one-way fluid valve, that may split expander passageway 167 into at least two distinct expander sub-passageways 167a and 167b and that may only fluidly couple second sub-passageway 167b to first sub-passageway 167a in one direction. For example, as shown in the transition of the geometry of the expanded state of assembly 100" from the equilibrium geometry of the expanded state of assembly 100" of FIGS. 11 and 13 (e.g., where only second sub-passageway 167b of distal expander component section 166c may be inflated from the uninflated state of assembly 100" of FIGS. 10 and 12 (e.g., via opening(s) 106 between passageway 117 and second sub-passageway 167b)) to a deformed geometry of the expanded state of assembly 100" of FIG. 14 and then to another deformed geometry of the expanded state of assembly 100" of FIG. 15, limiting mechanism 159" may be operative to pass a portion of the fluid from within second sub-passageway 167b (e.g., of distal expander component section 166c) through limiting mechanism 159" (e.g., in the direction of arrow OW of FIGS. 14 and 15) and into first sub-passageway 167a (e.g., of proximal expander component section 166a) when any suitable external force is applied to expander subassembly 160" (e.g., when opening 91 of patient 1 applies a constricting force (e.g., in the direction of arrows CW of FIG. 15) on a portion of distal expander component section 166c and thus on second sub-passageway 167b when a portion of distal expander component section 166c is pulled back through opening 91 in the direction of arrow R (e.g., such that different portions of distal expander component section 166c alone may straddle opening 91 for maintaining assembly 100" at the position of FIG. 14 within patient 1, and then such that distal expander component section 166c and proximal expander component section 166a may straddle opening 91 for maintaining assembly 100" at the position of FIG. 15 within patient 1)). After any suitable material is communicated between target space 95 and passageway 15 of patient 1 via assembly 100" in its expanded state of FIGS. 13-15, assembly 100" may be removed from patient 1 (e.g., in the direction of arrow R), for example, after removing at least a portion of the fluid in second sub-passageway 167b via opening(s) 106 and passageway 117 and opening 104 (e.g., such that a maximum cross-sectional dimension of second sub-passageway 167b may be less than that of opening 91) yet while potentially maintaining the fluid in first sub-passageway 167a of proximal expander component section 166a. In some embodiments, passageway 119 may be provided by two distinct passageways, a first of which may extend from an opening at or near proximal assembly end 101 to at least one opening 106 coupling that first distinct passageway to first sub-passageway 167a of proximal expander component section 166a of subassembly 160" and a second of which may extend from an opening at or near proximal assembly end 101 to at least one opening 106 coupling that second distinct passageway to second sub-passageway 167b of distal expander component section 166c of subassembly 160", such that proximal expander component section 166a and distal expander component section 166c may be independently inflated (e.g., after insertion of assembly 100" into patient 1) and/or deflated (e.g., prior to removal of assembly 100" from patient 1).

Figure 16:
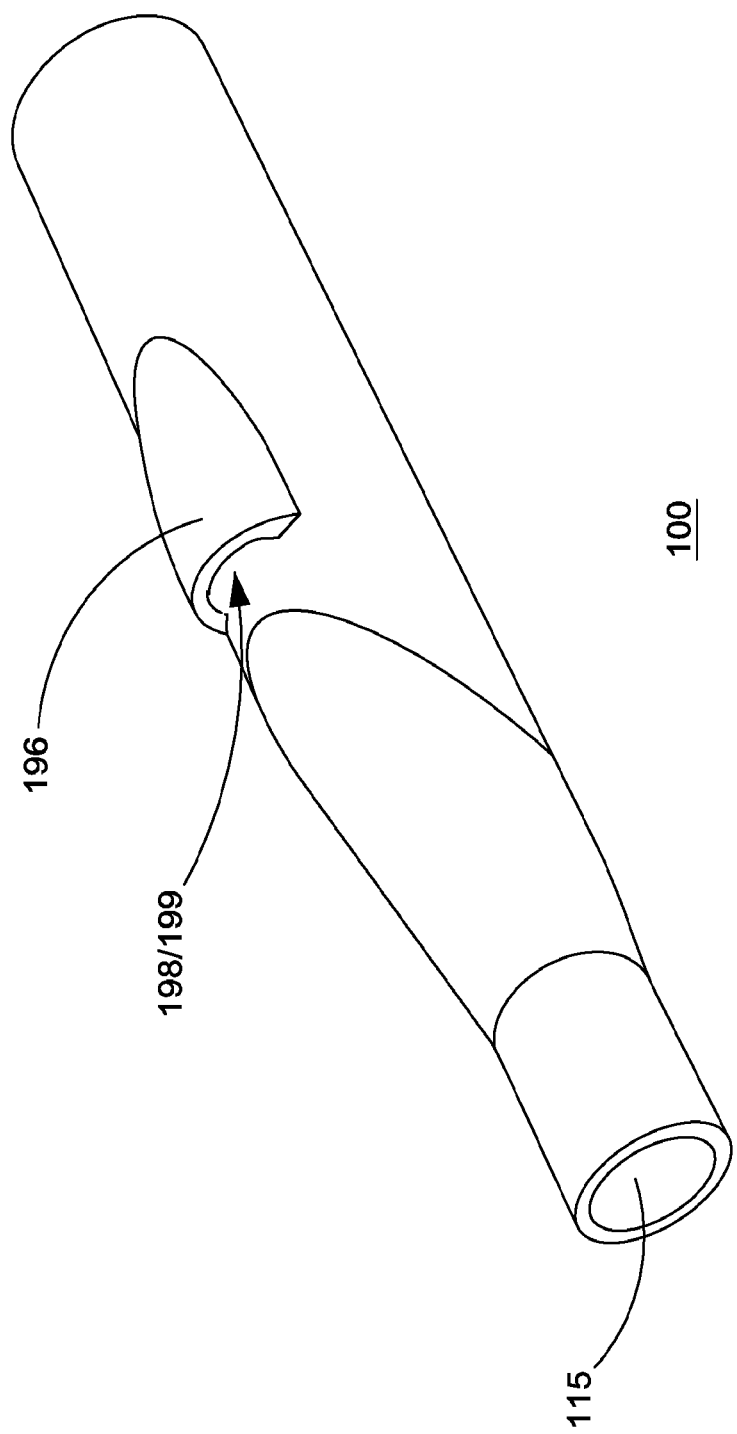
FIGS. 16 and 17 are different perspective views of a portion of the intubation assembly of FIGS. 2-7.
Figure 17:
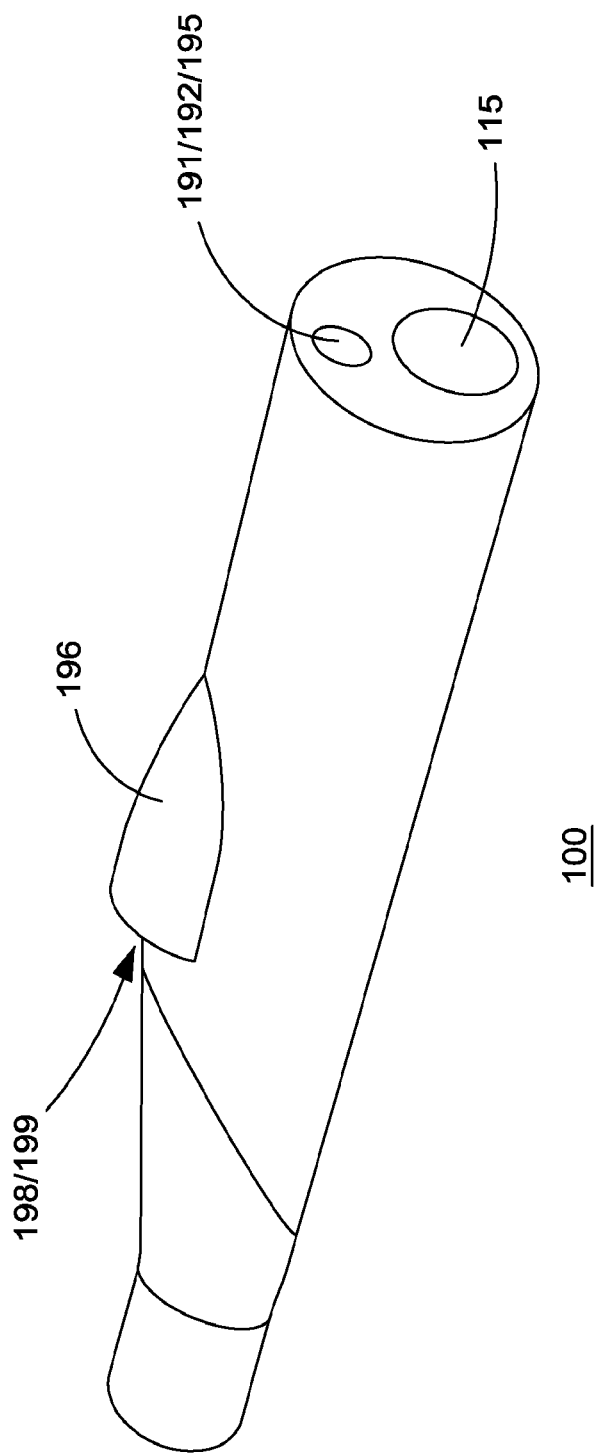
Figure 18:
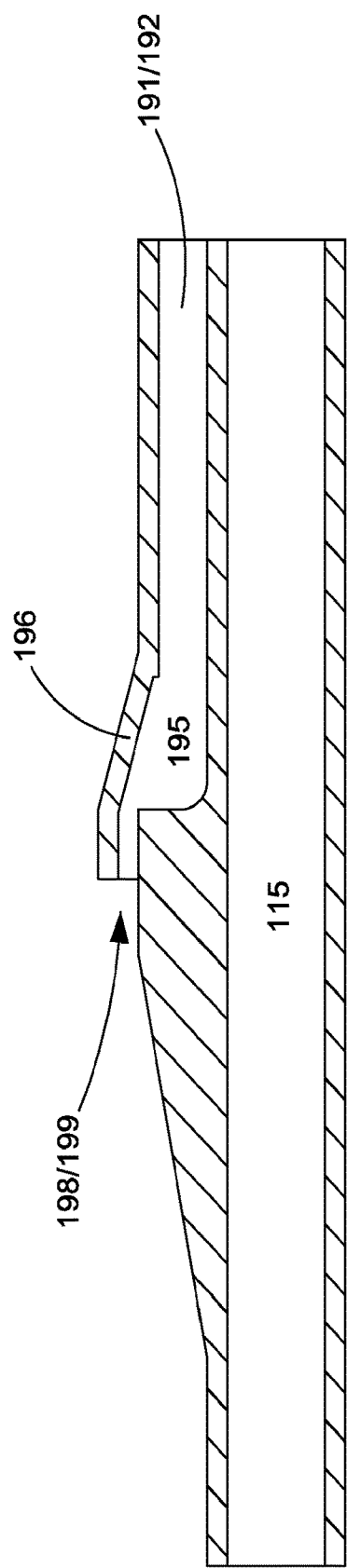
FIG. 18 is a cross-sectional view of the portion of the intubation assembly of FIGS. 16 and 17.
Figure 19:
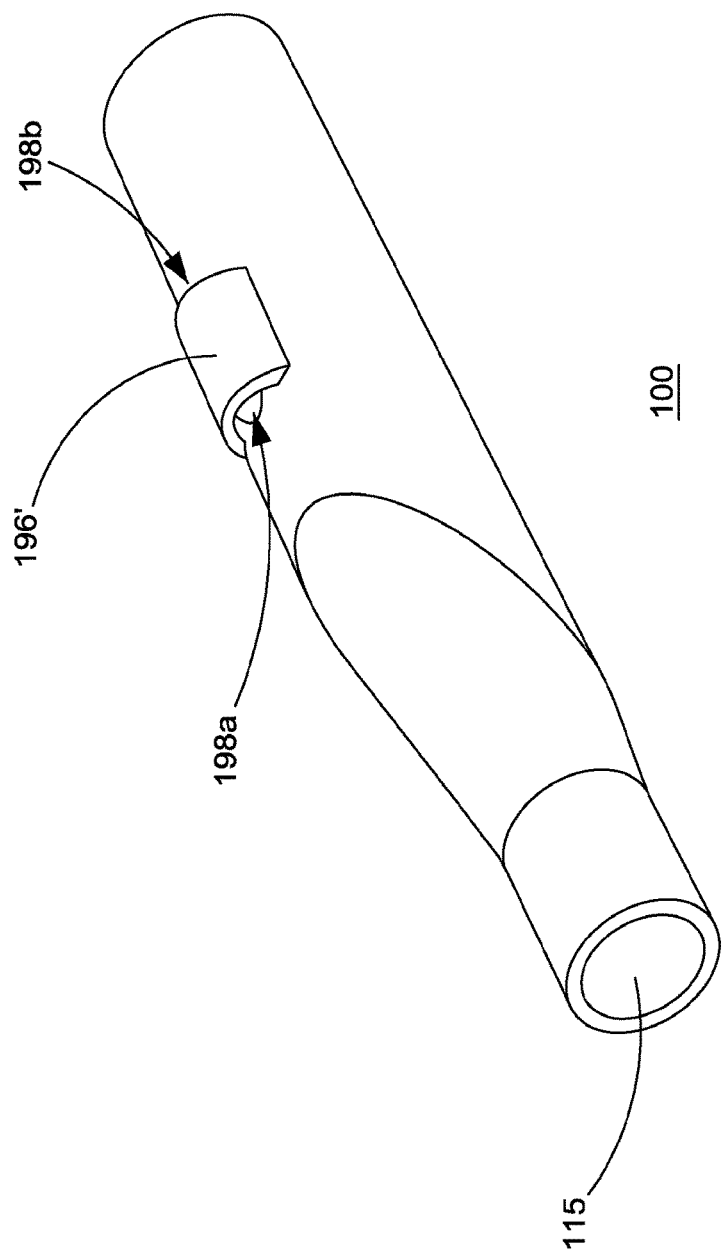
FIGS. 19 and 20 are different perspective views of an alternative portion of the intubation assembly of FIGS. 2-7.
Figure 20:
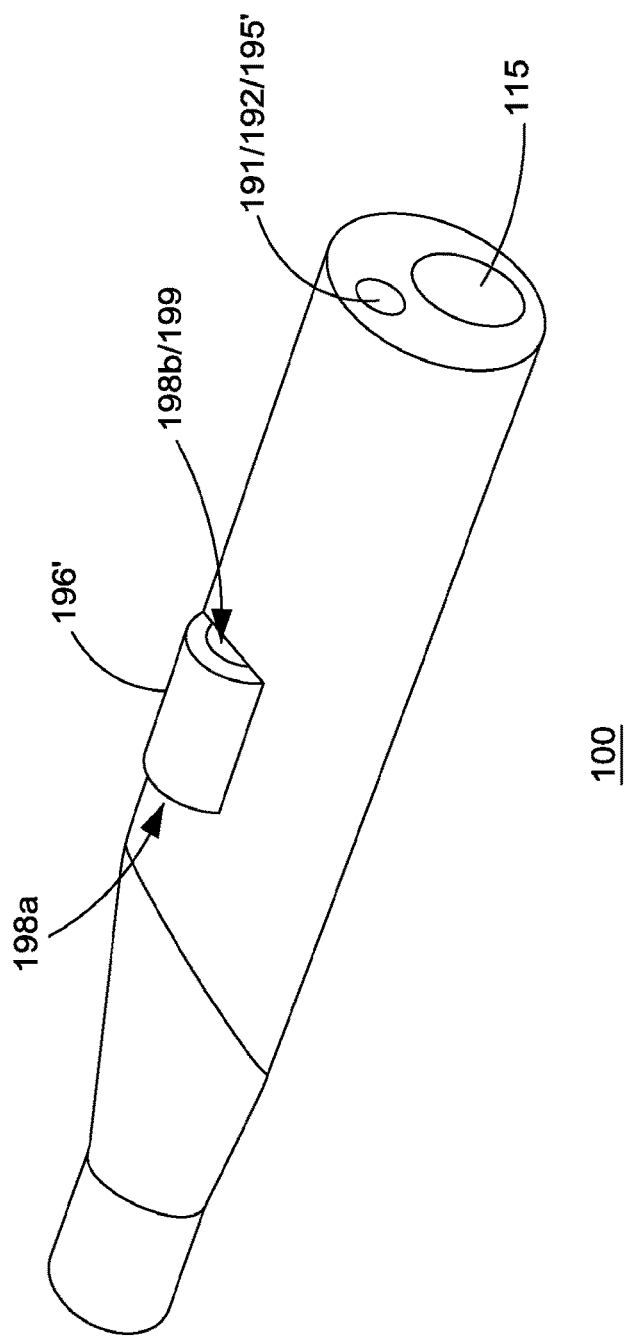
Figure 21:
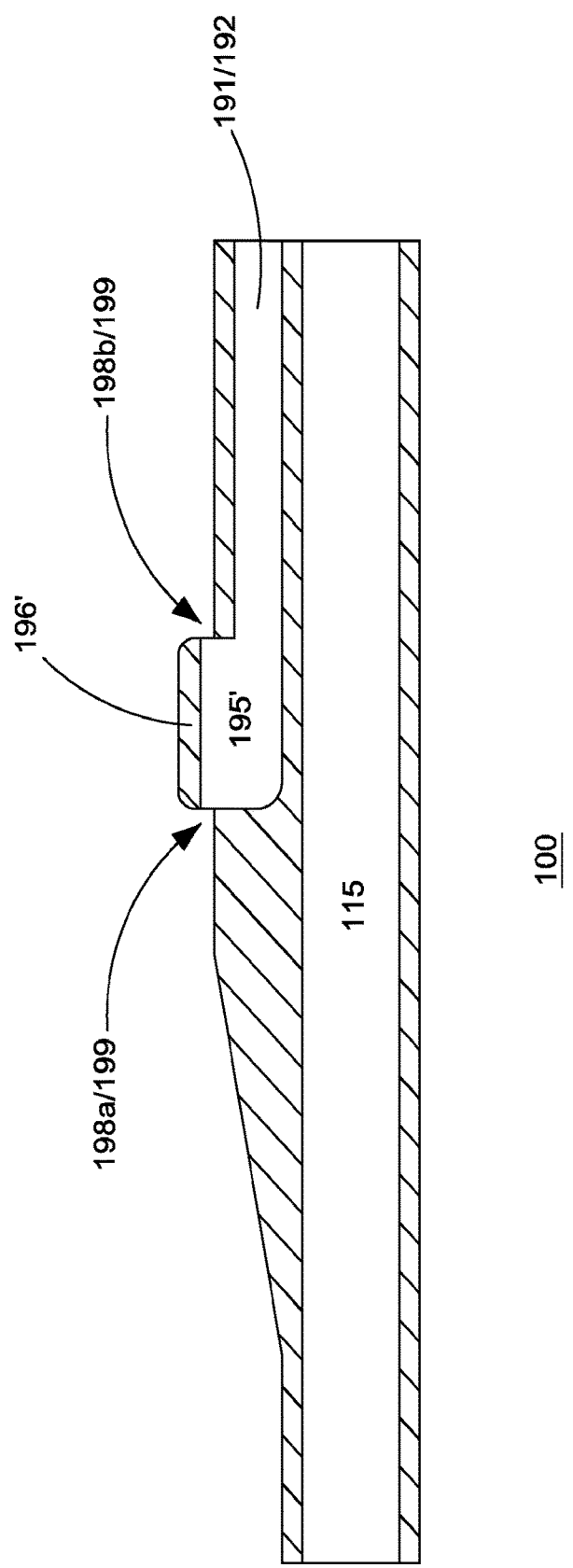
FIG. 21 is a cross-sectional view of the portion of the intubation assembly of FIGS. 19 and 20.
Figure 22A:
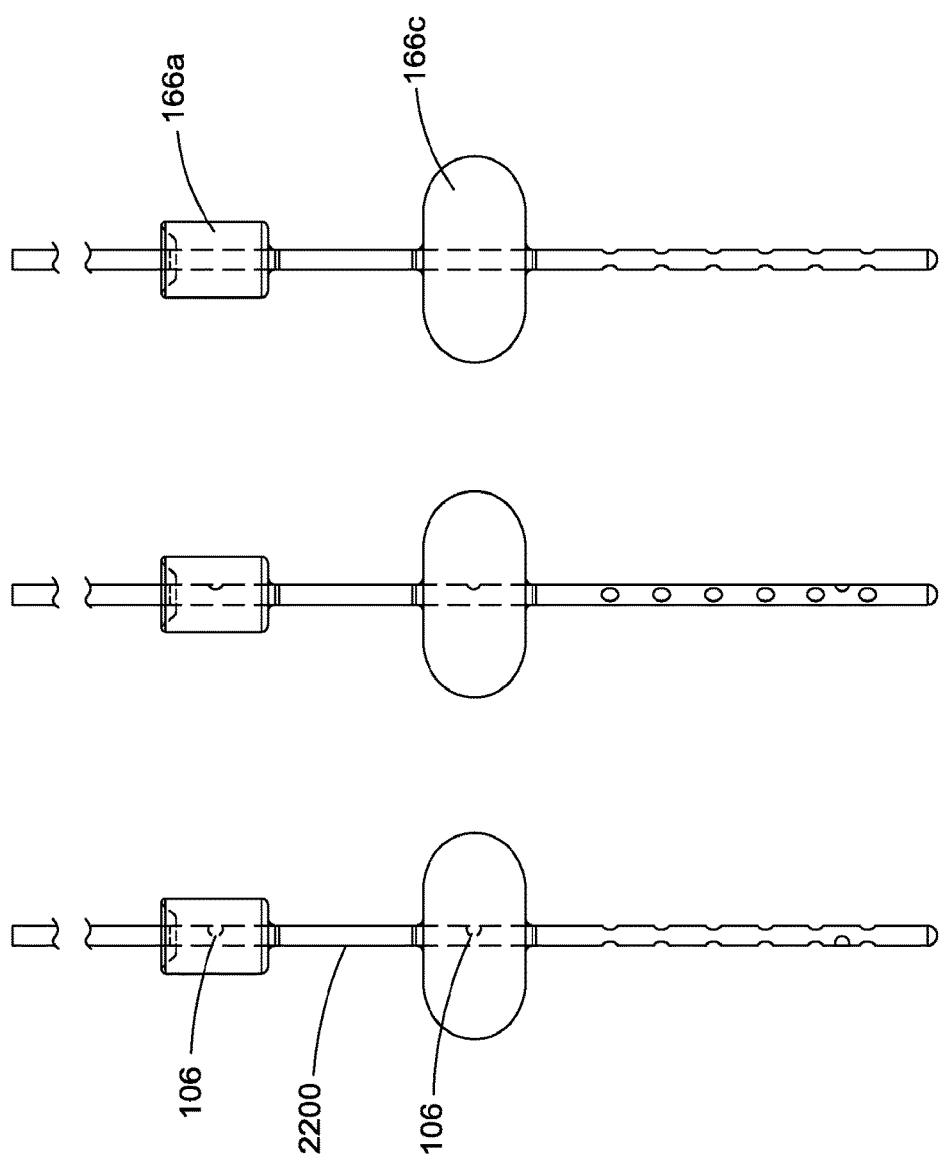
FIGS. 22A-22D depict side and cross-sectional views of the intubation assembly, in accordance with embodiments described herein.
Figure 22B:
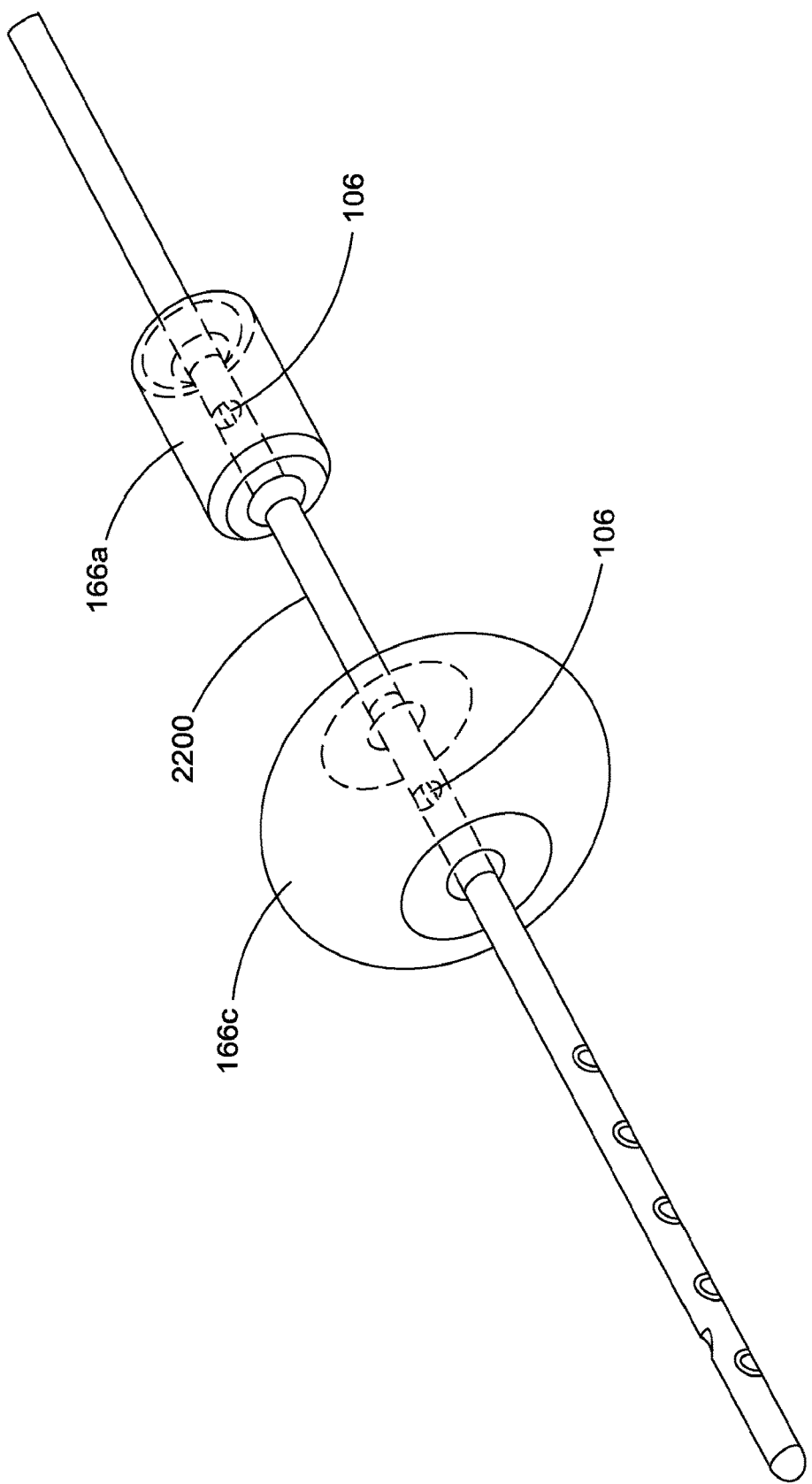
Figure 22C:
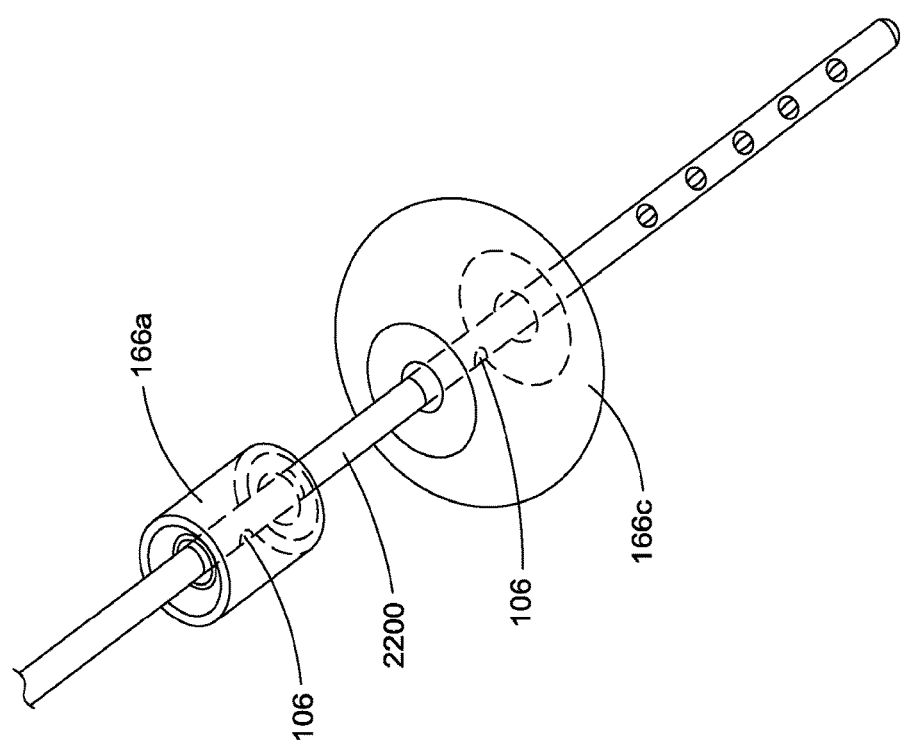
Figure 22D:
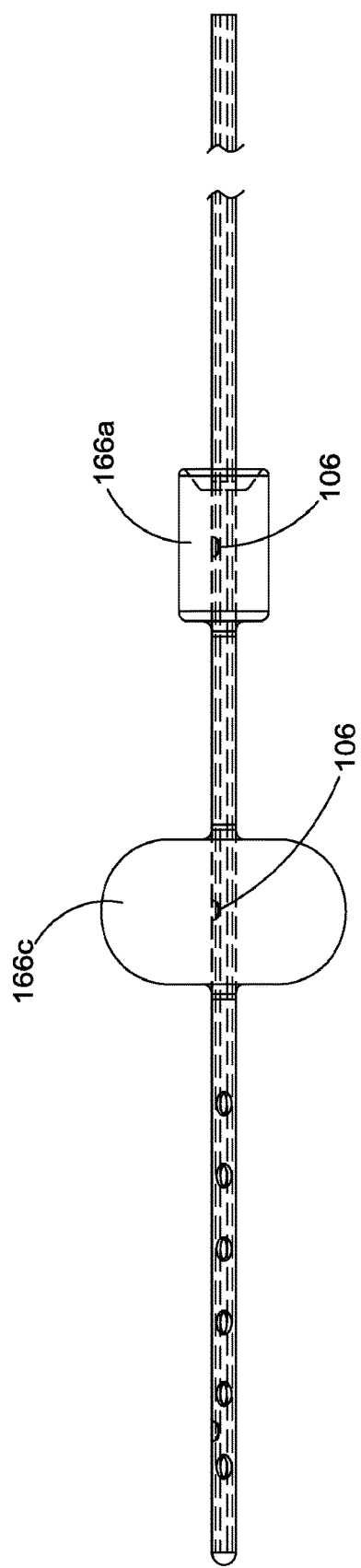

In some embodiments, as shown, for example, in FIGS. 2-3, assembly 100 may also include a supplemental tube passageway 195 that may be defined by at least a portion of one or more walls 113 of tube subassembly 110 that may be provided to treat (e.g., extract material from and/or inject material into) a supplemental region of patient 1 that may be proximal to target 95 and proximal to expander subassembly 160 when assembly 100 is in its expanded state in a functional position within patient 1 (e.g., the position of FIGS. 5-7). For example, as shown, supplemental tube passageway 195 may extend from a proximal end 191 to at least one distal end 199. A proximal opening 192 for passageway 195 may be provided at or near proximal end 191 and a distal opening 198 for passageway 195 may be provided at or near distal end 199. Fluid may be injected into patient 1 (e.g., by operator O) through passageway 195 from opening 192 to opening 198 and/or fluid may be removed from patient 1 (e.g., by operator O) through passageway 195 from opening 198 to opening 192. As shown, at least a portion of passageway 195 may be provided adjacent to passageway 119 and/or passageway 115. As shown in FIGS. 16-18 (without expander passageway 119), an external surface 196 of a wall defining at least a portion of supplemental tube passageway 195 may protrude out from a portion of surface 118 to expose opening 198 at end 199 in a direction facing the direction of expander subassembly 160 (e.g., in direction of arrow I for insertion of assembly 100 into a patient), where such a configuration of surface 196 may prevent direct contact between opening 198 and a wall 13 of patient 1 (e.g., to prevent direct suction on a wall of patient tissue) but instead surface 196 may contact patient 1 in certain situations of use. Alternatively, as shown in FIGS. 19-21 (without expander passageway 119), an external surface 196' of a wall defining at least a portion of a supplemental tube passageway 195' may protrude out from a portion of surface 118 to expose a first opening 198a at end 199 in a direction facing the direction of expander subassembly 160 (e.g., in direction of arrow I for insertion of assembly 100 into a patient, similar to opening 198 of FIGS. 16-18) as well as a second opening 198b at end 199 in a direction substantially opposite of first opening 198a (e.g., in direction of arrow R for removal of assembly 100 into a patient), where such a configuration of surface 196' may prevent direct contact between opening 198 and a wall 13 of patient 1 (e.g., to prevent direct suction on a wall of patient tissue) but instead surface 196 may contact patient 1 in certain situations of use while enabling multiple openings for fluid communication between supplemental tube passageway 195' and patient 1 (e.g., up and down along the axis of assembly 100).

Various materials may be used for various elements of an assembly 100, which may vary based on the procedure and/or patient in which assembly 100 is to be used. As just one example, when assembly 100 may be used for a nasogastric intubation procedure, tube subassembly 110 may be made of polyurethane, silicone, polyvinyl chloride, or rubber, expander subassembly 160 may be a molded piece and/or extruded piece and/or may be made of silicone, polyurethane, rubber, thermoplastic elastomers, or the like and/or may be coupled to tube subassembly 110 via any suitable type of mechanism or crimp or bond or adhesive (e.g., cyanoacrylate or silicone glue). One or more of any or all portions of expander subassembly 160 and tube subassembly 110, and/or the like of assembly 100 may be provided with an alkaline coating on one or both of its interior and exterior walls, such that when material (e.g., food or acidic stomach contents) travels through such components, the acidity of the material may get neutralized. Additionally or alternatively, one or more of any or all portions of expander subassembly 160 and tube subassembly 110, and/or the like of assembly 100 may be at least partially X-ray visible such that an operator may ensure that it is properly placed within patient 1 for a particular procedure.

While there have been described expandable assemblies and methods for using and making the same, it is to be understood that many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. It is also to be understood that various directional and orientational terms such as "proximal" and "distal," "up" and "down," "front" and "back," "top" and "bottom" and "side," "length" and "width" and "thickness" and "diameter" and "cross-section" and "longitudinal," "X-" and "Y-" and "Z-," and the like that may be used herein only for convenience, and that no fixed or absolute directional or orientational limitations are intended by the use of these words. For example, the assemblies and patients can have any desired orientations. If reoriented, different directional or orientational terms may need to be used in their description, but that will not alter their fundamental nature as within the scope and spirit of the subject matter described herein in any way.

Therefore, those skilled in the art will appreciate that the invention can be practiced by other than the described embodiments, which are presented for purposes of illustration rather than of limitation.

What is claimed is:

1. An expandable nasogastric intubation assembly, comprising:
    a tube subassembly, comprising:
        at least one tube wall defining at least one internal passageway extending along at least a portion of the intubation assembly, the at least one tube wall comprising one or more surfaces that in conjunction with the at least one tube wall define a second passageway beginning at a closed end and extending to a passageway access opening;
        a proximal tube opening located at a proximal end of the intubation assembly; and
        a distal tube opening located at a distal end of the intubation assembly,
        wherein the passageway access opening is radially adjacent to the proximal tube opening; and
    an expander subassembly, comprising:
        an inflatable balloon comprising a proximal expander component section and a distal expander component section; and
        at least one one-way valve located between the proximal expander component section and the distal expander component section,
        wherein the proximal expander component section is located between the proximal end of the intubation assembly and the distal expander component section; and
        wherein the distal expander component section is located between the distal end of the intubation assembly and the proximal expander component section,
    wherein the inflatable balloon is coupled to the tube subassembly, the proximal expander component section is configured to be inflated from an injection of fluid into at least one first opening located in the second passageway, and the distal expander component section is configured to be inflated by the injection of fluid into at least one second opening located in the second passageway; and
    wherein when one or more patient walls contract against the expander subassembly the injectable fluid flows from the distal expander component section into the proximal expander component section.

2. The assembly as recited in claim 1, wherein the distal expander component section has a cross-sectional dimension greater than a cross-sectional dimension of the proximate expander component section.

3. The assembly as recited in claim 1, wherein the proximal expander component section and the distal expander component section are separated by a non-expanding portion of the at least one tube wall.

4. The assembly as recited in claim 1, wherein the proximal expander component section and the distal expander component section are separated by an intermediate expander component section;
    wherein the intermediate expander component section is constricted such that the intermediate expander component section has a cross-sectional dimension less than that of the proximate expander component section.

5. The assembly as recited in claim 1, wherein the injected fluid is air.

6. The assembly as recited in claim 1, the expander subassembly further comprising:
    at least one second one-way valve on the at least one second opening located on the second passageway;
    wherein when one or more patient walls contract against the proximal expander component section the injectable fluid flows from the proximal expander component section through the second passageway and into the distal expander component section.

7. An expandable nasogastric intubation assembly, comprising:
    a tube subassembly, comprising:
        at least one tube wall defining at least one internal passageway extending along at least a portion of the intubation assembly, the at least one tube wall comprising one or more surfaces that in conjunction with the at least one tube wall define a second passageway beginning at a closed end and extending to a passageway access opening;
        a proximal tube opening located at a proximal end of the intubation assembly;
        a distal tube opening located at a distal end of the intubation assembly; and
        a burst valve located across the passageway access opening,
        wherein the passageway access opening is radially adjacent to the proximal tube opening; and
    an expander subassembly, comprising:
        an inflatable balloon comprising a proximal expander component section and a distal expander component section,
        wherein the proximal expander component section is located between the proximal end of the intubation assembly and the distal expander component section; and
        wherein the distal expander component section is located between the distal end of the intubation assembly and the proximal expander component section,
    wherein the inflatable balloon is coupled to the tube subassembly, the proximal expander component section is configured to be inflated from an injection of fluid into at least one first opening located in the second passageway, and the distal expander component section is configured to be inflated by the injection of fluid into at least one second opening located in the second passageway; and
    wherein the burst valve is configured to release if the proximal expander component section and the distal expander component section are inflated to a maximum cross-sectional dimension and one or more patient walls contract against the expander subassembly.

8. The assembly as recited in claim 1, the tube subassembly further comprising:
    a supplemental tube passageway embedded within the at least one tube wall.

9. An expandable nasogastric intubation assembly, comprising:
    a tube subassembly, comprising:
        at least one tube wall defining at least one internal passageway extending along at least a portion of the intubation assembly, the at least one tube wall comprising one or more surfaces that in conjunction with the at least one tube wall define a second passageway beginning at a closed end and extending to a passageway access opening;

a proximal tube opening located at a proximal end of the intubation assembly; and a distal tube opening located at a distal end of the intubation assembly; and a burst valve located across the passageway access opening, wherein the passageway access opening is radially adjacent to the proximal tube opening; and an expander subassembly coupled to the tube subassembly, comprising:

a proximal expander component comprising a first limiting mechanism secured to an end of the proximal expander component and a portion of the at least one tube wall; and a distal expander component comprising a second limiting mechanism secured to an end of the distal expander component and a portion of the at least one tube wall, wherein the proximal expander component is located between the proximal end of the intubation assembly and the distal expander component; and wherein the distal expander component is located between the distal end of the intubation assembly and the proximal expander component, wherein the proximal expander component is configured to be inflated from an injection of fluid into at least one first opening located in the second passageway, and the distal expander component is configured to be inflated by the injection of fluid into at least one second opening located in the second passageway; and wherein the burst valve is configured to release if the proximal expander component and the distal expander component are inflated to a maximum cross-sectional dimension and one or more patient walls contract against the expander subassembly.

10. The assembly as recited in claim 9, wherein the distal expander component has a cross-sectional dimension greater than a cross-sectional dimension of the proximal expander component.

11. The assembly as recited in claim 9, wherein the proximal expander component and the distal expander component are separated by a length of non-expanding tube wall.

12. The assembly as recited in claim 9, wherein the injected fluid is air.

13. The assembly as recited in claim 9, wherein when one or more patient walls contract against the proximal expander component the injectable fluid flows from the proximal expander component into the distal expander component; and wherein when one or more patient walls contract against the distal expander component the injectable fluid flows from the distal expander component through the second passageway and into the proximal expander component.

14. The assembly as recited in claim 9, the tube subassembly further comprising:

a supplemental tube passageway embedded within the at least one tube wall.

* * * * *